United States Patent
Askew et al.

(10) Patent No.: US 9,662,331 B2
(45) Date of Patent: *May 30, 2017

(54) 3-ARYL-2-((ARYLAMINO)METHYL) QUINAZOLIN-4-(3H)-ONES

(71) Applicant: SciFluor Life Sciences, Inc., Cambridge, MA (US)

(72) Inventors: Ben C. Askew, Marshfield, MA (US); Takeru Furuya, Cambridge, MA (US)

(73) Assignee: SciFluor Life Sciences, Inc., Cambridge, MA (US)

( * ) Notice: Subject to any disclaimer, the term of this patent is extended or adjusted under 35 U.S.C. 154(b) by 6 days.

This patent is subject to a terminal disclaimer.

(21) Appl. No.: 14/940,230

(22) Filed: Nov. 13, 2015

(65) Prior Publication Data
US 2016/0067249 A1   Mar. 10, 2016

Related U.S. Application Data

(63) Continuation of application No. 14/228,876, filed on Mar. 28, 2014, now Pat. No. 9,216,985.

(60) Provisional application No. 61/806,155, filed on Mar. 28, 2013.

(51) Int. Cl.
| | | |
|---|---|---|
| *A61K 31/517* | (2006.01) | |
| *C07D 487/04* | (2006.01) | |
| *C07D 473/34* | (2006.01) | |
| *C07D 471/04* | (2006.01) | |
| *A61K 31/519* | (2006.01) | |
| *A61K 31/52* | (2006.01) | |

(52) U.S. Cl.
CPC .......... *A61K 31/517* (2013.01); *A61K 31/519* (2013.01); *A61K 31/52* (2013.01); *C07D 471/04* (2013.01); *C07D 473/34* (2013.01); *C07D 487/04* (2013.01)

(58) Field of Classification Search
CPC .................................................. A61K 31/517
See application file for complete search history.

(56) References Cited

PUBLICATIONS

Ihle, N., et al. "Take your PIK: phosphatidylinositol 3-kinases inhibitors race through the clinic and toward cancer therapy." Mol. Cancer Ther. (Jan. 2009.*
Mayo Clinic. "Cancer." © 2016. Available from: < http://www.mayoclinic.org/diseases-conditions/cancer/basics/prevention/CON-20032378?p=1 >.*
Fruman, D., et al. "PI3Kδ Inhibitors in Cancer: Rationale and Serendipity Merge in the Clinic." (Dec. 2011), vol. 1, p. 562-572.*
American Cancer Society. "Cancer Types." © 2013. Available from: http://www.cancer.org/cancer/showallcancertypes/index.
Fruman, D., et al. "PI3Kδ Inhibitors in Cancer: Rationale and Serendipity Merge in the Clinic" (Dec. 2011), vol. 1, p. 562-572.
Ihle, N., et al. Take your PIK: phosphatidylinositol 3-kinases inhibitors race through the clinic and toward cancer therapy. Mol. Cancer Ther. (Jan. 2009), vol. 8, Issue 1, pp. 1-9.
Lasalle.edu "Common bonding for carbon, nitrogen and oxygen." (c) Jun. 10, 2010. Available from: http:/ /web.archive.org/web/20100610125737/http://www.lasalle.edu/~price/201%20bonding%20for%20C%20N%200.pdf.
National Cancer Institute, "Cancer Prevention Overview," © Apr. 17, 2004. Available from: http://www.cancer.gov/cancertopics/pdq/prevention/overview/patient/page3/print.
Navigating Cancer. "List of Cancer Chemotherapy Drugs," © 2013. Available from: https://www.navigatingcancer.com/library/all/chemotherapy_drugs.

* cited by examiner

*Primary Examiner* — Noble Jarrell
*Assistant Examiner* — John S Kenyon
(74) *Attorney, Agent, or Firm* — Cooley LLP; Ivor R. Elrifi; Heidi A. Erlacher

(57) ABSTRACT

The invention relates to novel quinazolinone compounds and their use as inhibitors of PI3 kinases, for example, PI3Kδ, for treating and/or preventing diseases, disorder, and conditions associated with modulating PI3 kinase activity. Novel 3-aryl-2-((arylamino)methyl)quinazolin-4(3H)-one derivatives and pharmaceutically acceptable salts or solvates thereof and their use for the treatment or prevention of diseases, disorders, and conditions associated with the activity of one or more PI3 kinase, such as PI3Kδ, are disclosed.

17 Claims, No Drawings

3-ARYL-2-((ARYLAMINO)METHYL) QUINAZOLIN-4-(3H)-ONES

CROSS-REFERENCE TO RELATED APPLICATION

This application is a continuation of U.S. Ser. No. 14/228,876, filed on Mar. 28, 2014 (now allowed), which claims priority to and the benefit of U.S. Ser. No. 61/806,155, filed on Mar. 28, 2013, the entire contents of each of which are incorporated herein by reference.

BACKGROUND

Phosphoinositide 3-kinases (PI3Ks) are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The PI3Ks signaling pathway is one of the most highly mutated systems in human cancers. PI3K signaling is also a key factor in many other diseases in humans. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are prime targets for the development of new therapeutics. There remains a need for PI3K inhibitors suitable for drug development. The present invention addresses this need and provides related advantages as well by providing new classes of PI3 kinase inhibitors.

SUMMARY OF THE INVENTION

The present invention relates to quinazolinone compounds and methods of preparing these compounds. Specifically, the present invention provides a compound of Formula I:

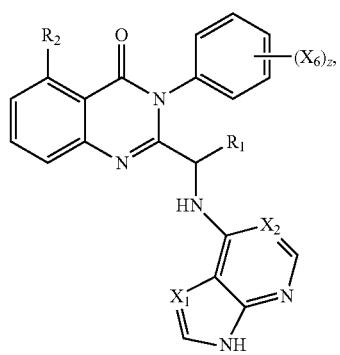

(I)

or a pharmaceutically acceptable salt or solvate thereof. In Formula I, the variables $X_1$, $X_2$, $X_6$, z, $R_1$, and $R_2$ can be selected from the respective groups of chemical moieties defined herein.

The present invention also relates to a pharmaceutical composition comprising a compound of any of the formulae described herein or a pharmaceutically acceptable salt or solvate thereof, and a pharmaceutically acceptable carrier or excipient.

The present invention also relates to methods of treating or preventing a disease or disorder mediated by the activity of one or more PI3 kinases by administering to a subject in need thereof, a therapeutically effective amount of a compound of any of the formulae described herein, or a pharmaceutically acceptable salt or solvate thereof, in combination with a pharmaceutically acceptable carrier or excipient, such that the disease or disorder is treated.

The present invention also relates to the manufacture of a medicament for treating or preventing a disease or disorder mediated by the activity of one or more PI3 kinases, wherein the medicament comprises a compound of any of the formulae described herein or a pharmaceutically acceptable salt or solvate thereof.

The present invention also relates to a composition for use in a method for treating or preventing a disease or disorder mediated by the activity of one or more PI3 kinases, wherein the composition comprises a compound of any of the formulae described herein or a pharmaceutically acceptable salt or solvate thereof.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

DETAILED DESCRIPTION OF THE INVENTION

For purposes of the present invention, the following definitions will be used (unless expressly stated otherwise):

The term "a compound of the invention" or "compounds of the invention" refers to a compound(s) disclosed herein, e.g., a compound(s) of the invention includes a compound(s) of any of the formulae described herein, including Formulae I, Ia, II, and IIa, and/or a compound(s) explicitly disclosed herein. Whenever the term is used in the context of the present invention it is to be understood that the reference is being made to the free base and deuterium labeled compounds, and the corresponding pharmaceutically acceptable salts or solvates thereof, provided that such is possible and/or appropriate under the circumstances.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient, and salt must be compatible with the active ingredient of the formulation (e.g., a compound of the invention). It is understood by those of ordinary skill in this art that the terms "pharmaceutical formulation" and "pharmaceutical composition" are generally interchangeable, and they are so used for the purposes of this application.

Some of the compounds of the present invention may exist in unsolvated as well as solvated forms such as, for example, hydrates.

"Solvate" means a solvent addition form that contains either a stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates, or trihydrates. Equally suitable are the hydrates of salts of the compounds of the invention.

The invention also includes metabolites of the compounds described herein.

Physiologically acceptable, i.e., pharmaceutically compatible, salts can be salts of the compounds of the invention with inorganic or organic acids. Preference is given to salts with inorganic acids, such as, for example, hydrochloric acid, hydrobromic acid, phosphoric acid, or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, or benzoic acid, or methanesulphonic acid, ethanesulphonic acid, benzenesulphonic acid, toluenesulphonic acid, or naphthalenedisulphonic acid.

Other pharmaceutically compatible salts which may be mentioned are salts with customary bases, such as, for example, alkali metal salts (for example sodium or potassium salts), alkaline earth metal salts (for example calcium or magnesium salts), or ammonium salts, derived from ammonia or organic amines, such as, for example, diethylamine, triethylamine, ethyldiisopropylamine, procaine, dibenzylamine, N-methylmorpholine, dihydroabietylamine, or methylpiperidine.

When any variable (e.g., X) occurs more than one time in any constituent or formula for a compound, its definition at each occurrence is independent of its definition at every other occurrence. Thus, for example, if a group is shown to be substituted with one or more X moieties, then X at each occurrence is selected independently from the definition of X. Also, combinations of substituents and/or variables are permissible, but only if such combinations result in stable compounds within a designated atom's normal valency.

As used herein, the term "treat," "treating," or "treatment" herein, is meant decreasing the symptoms, markers, and/or any negative effects of a disease, disorder, and/or condition in any appreciable degree in a patient who currently has the disease, disorder, and/or condition. In some embodiments, treatment may be administered to a subject who exhibits only early signs of the condition for the purpose of decreasing the risk of developing the disease, disorder, and/or condition.

As used herein, the term "prevent," "prevention," or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, "subject" means a human or animal (in the case of an animal, more typically a mammal). In one aspect, the subject is a human. In one aspect, the subject is a male. In one aspect, the subject is a female.

"Isomers" are different compounds that have the same molecular formula. "Stereoisomers" are isomers that differ only in the way the atoms are arranged in space, i.e., having a different stereochemical configuration. "Enantiomers" are a pair of stereoisomers that are non-superimposable mirror images of each other. A 1:1 mixture of a pair of enantiomers is a "racemic" mixture. The term "(+/−)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms, and intermediate mixtures. Optically active (R)- and (S)- isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4- dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" (LG) is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy, and tosyloxy groups.

"Protecting group" (PG) has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999). For example, a hydroxy protected form is where at least one of the hydroxy groups present in a compound is protected with a hydroxy protecting group. Likewise, amines and other reactive groups may similarly be protected.

The problem to be solved by the present invention is the identification of novel compounds for the treatment and/or prevention of an inflammatory disease, autoimmune disease, respiratory disease, hyperproliferative disorder, cardiovascular disease, disease of the bone, reperfusion injury, central nervous system (CNS) disorder, and/or other conditions mediated by the activity of one or more PI3 kinases, such as PI3Kδ. The PI3 kinase family comprises 15 kinases with distinct substrate specificities, expression patterns, and modes of regulation. Inhibitors against PI3 kinase enzymes have been discovered and proved to be helpful tools for deciphering enzyme function. However, many of the available PI3K inhibitors are not suitable for administering to patients for a variety of reasons. In some instances, PI3K inhibitors are associated with adverse effects. Further, PI3K inhibitors, which are pan-PI3K inhibitors, lack isoform specificity and may cause off-target effects. For example, some PI3K inhibitors are believed to be associated with an increased incidence of insulin resistance. Other adverse side effects related to PI3K inhibitors include hyperglycemia, gastrointestinal toxicity, pneumonia, neutropenia, thrombocytopenia, anemia, transaminase elevation, nausea, fatigue, and rash. The invention provides the solution of new 3-aryl-2-((arylamino)methyl)quinazolin-4(3H)-one compounds for treating inflammatory disease, autoimmune disease, respiratory disease, hyperproliferative disorder, cardiovascular disease, disease of the bone, reperfusion injury, central nervous system (CNS) disorder, and/or other conditions mediated by the activity of one or more PI3 kinases, such as PI3Kδ. The compounds described herein have the advantage of providing improved potency, selectivity, isoform specificity, tissue penetration, half-life, and/or metabolic stability. In one aspect, compounds described herein have superior brain penetration.

Compounds of the Invention

The present invention relates to novel quinazolinone compounds and their uses. The present invention relates to the synthesis of novel quinazolinone compounds.

The invention provides a compound of Formula I or Ia:

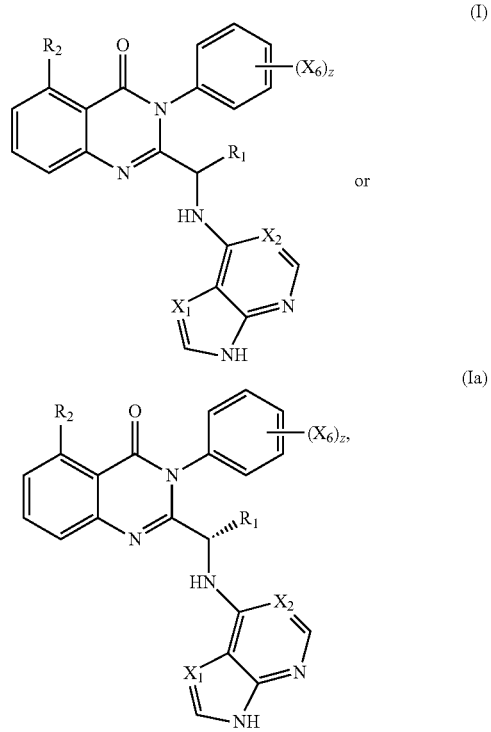

or a pharmaceutically acceptable salt or solvate thereof, wherein:

$X_1$ is selected from N, CH, CF, $CCF_3$, $CCHF_2$, and $CCH_2F$;

$X_2$ is N or CH;

$R_1$ is $(CX_{3A}X_{4A})_s$—$(O)_v$—$(CX_{3B}X_{4B})_t$—$(O)_w$—$(CX_{3C}X_{4C})_u$—$(O)_x$—$X_5$;

$X_{3A}$, $X_{3B}$, $X_{3C}$, $X_{4A}$, $X_{4B}$, and $X_{4C}$ are each independently selected from H and F;

$X_5$ is selected from H, F, $CF_3$, $CHF_2$, $CH_2F$, $OCF_3$, $OCHF_2$, $OCH_2F$, $OCH_2CF_3$, $OCH_2CHF_2$, and $OCH_2CH_2F$;

s, t, and u are each independently selected from 0, 1, 2, 3, 4, 5, 6, and 7;

v, w, and x are each independently selected from 0 and 1;

$R_2$ is Cl or F;

each $X_6$ is independently $(CX_{7A}X_{8A})_e$—$(O)_h$—$(CX_{7B}X_{8B})_f$—$(O)_i$—$(CX_{7C}X_{8C})_g$—$(O)_j$—$X_9$;

$X_{7A}$, $X_{7B}$, $X_{7C}$, $X_{8A}$, $X_{8B}$, and $X_{8C}$ are each independently selected from H and F;

$X_9$ is selected from H, F, $CF_3$, $CHF_2$, $CH_2F$, $OCF_3$, $OCHF_2$, $OCH_2F$, $OCH_2CF_3$, $OCH_2CHF_2$, and $OCH_2CH_2F$;

e, f, and g are each independently selected from 0, 1, 2, 3, 4, 5, 6, and 7;

h, i, and j are each independently selected from 0 and 1; and z is selected from 0, 1, and 2, provided that when $X_1$ and $X_2$ are each N and z is 0, then $R_1$ comprises at least one F atom; and that when $X_1$ and $X_2$ are each N and $R_2$ is Cl, then z is 1 or 2 and $X_9$ is selected from $CF_3$, $CHF_2$, $CH_2F$, $OCF_3$, $OCHF_2$, $OCH_2F$, $OCH_2CF_3$, $OCH_2CHF_2$, and $OCH_2CH_2F$, and provided that $R_1$ does not contain a total number of more than 8 atoms of carbon and oxygen and $R_1$ does not contain adjacent oxygen atoms, and that each $X_6$ does not contain a total number of more than 8 atoms of carbon and oxygen and $X_6$ does not contain adjacent oxygen atoms.

In one aspect, the invention provides a compound of Formula I or Ia, wherein:
1a) $R_2$ is F; or
1b) $R_2$ is Cl.

In one aspect, the invention provides a compound of Formula II or IIa:

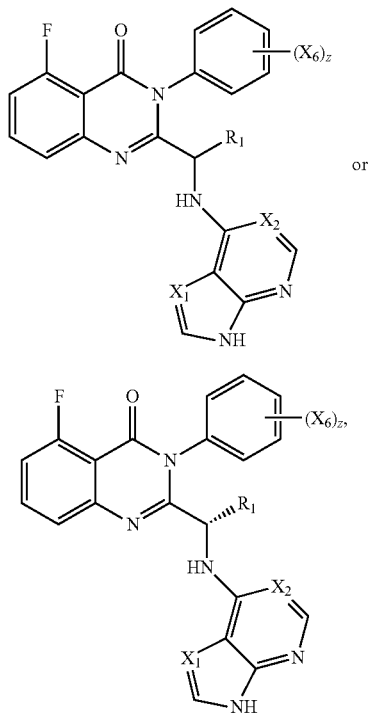

or a pharmaceutically acceptable salt or solvate thereof, wherein $R_1$, $X_1$, $X_2$, $X_6$, and z are each as defined hereinabove.

In one aspect, the invention provides a compound of Formula I, Ia, II, or IIa, wherein:
2a) $X_1$ is N and $X_2$ is N or CH;
  2ai) $X_1$ is N and $X_2$ is N; or
  2aii) $X_1$ is N and $X_2$ is CH;
2b) $X_1$ is CH and $X_2$ is N or CH;
  2bi) $X_1$ is CH and $X_2$ is N; or
  2bii) $X_1$ is CH and $X_2$ is CH; or
2c) $X_1$ is CF, $CCF_3$, $CCHF_2$, or $CCH_2F$ and $X_2$ is N or CH;
  2ci) $X_1$ is CF and $X_2$ is N;
  2cii) $X_1$ is CF and $X_2$ is CH;
  2ciii) $X_1$ is $CCF_3$ and $X_2$ is N; or
  2civ) $X_1$ is $CCF_3$ and $X_2$ is CH.

In one aspect, the invention provides a compound of Formula I, Ia, II, or IIa, wherein:
3a) the sum of v+w+x is 3;
3b) the sum of v+w+x≤2;
3c) the sum of v+w+x is 0 or 1;
3d) the sum of v+w+x is 1;
  3di) v is 1, w is 0, and x is 0;
  3dii) v is 0, w is 1, and x is 0; or
  3diii) v is 0, w is 0, and x is 1; or
3e) the sum of v+w+x is 0.

In one aspect, the invention provides a compound of Formula I, Ia, II, or IIa, wherein:
4a) the sum of s+t+u≤6;
4b) the sum of s+t+u is 6;
4c) the sum of s+t+u is 5;
4d) the sum of s+t+u is 4;
4e) the sum of s+t+u is 3;
4f) the sum of s+t+u is 2;
  4fi) s is 1, t is 1, and u is 0;
  4fii) s is 1, t is 0, and u is 1;
  4fiii) s is 0, t is 1, and u is 1;
  4fiv) s is 2, t is 0, and u is 0;
  4fv) s is 0, t is 2, and u is 0; or
  4fvi) s is 0, t is 0, and u is 2;
4g) the sum of s+t+u is 1;
  4gi) s is 1, t is 0, and u is 0;
  4gii) s is 0, t is 1, and u is 0; or
  4giii) s is 0, t is 0, and u is 1; or
4h) the sum of s+t+u is 0.

In one aspect, the invention provides a compound of Formula I, Ia, II, or IIa, wherein:
5a) $X_{3A}$, $X_{3B}$, $X_{3C}$, $X_{4A}$, $X_{4B}$, and $X_{4C}$ are each H;
5b) $X_{3A}$, $X_{3B}$, $X_{3C}$, $X_{4A}$, $X_{4B}$, and $X_{4C}$ are each F;
5c) one of $X_{3A}$, $X_{3B}$, $X_{3C}$, $X_{4A}$, $X_{4B}$, and $X_{4C}$ is F and the remaining $X_{3A}$, $X_{3B}$, $X_{3C}$, $X_{4A}$, $X_{4B}$, and $X_{4C}$ are H;
5d) two of $X_{3A}$, $X_{3B}$, $X_{3C}$, $X_{4A}$, $X_{4B}$, and $X_{4C}$ are F and the remaining $X_{3A}$, $X_{3B}$, $X_{3C}$, $X_{4A}$, $X_{4B}$, and $X_{4C}$ are H;
5e) three of $X_{3A}$, $X_{3B}$, $X_{3C}$, $X_{4A}$, $X_{4B}$, and $X_{4C}$ are F and the remaining $X_{3A}$, $X_{3B}$, $X_{3C}$, $X_{4A}$, $X_{4B}$, and $X_{4C}$ are H;
5f) four of $X_{3A}$, $X_{3B}$, $X_{3C}$, $X_{4A}$, $X_{4B}$, and $X_{4C}$ are F and the remaining $X_{3A}$, $X_{3B}$, $X_{3C}$, $X_{4A}$, $X_{4B}$, and $X_{4C}$ are H; or
5g) five of $X_{3A}$, $X_{3B}$, $X_{3C}$, $X_{4A}$, $X_{4B}$, and $X_{4C}$ are F and the remaining $X_{3A}$, $X_{3B}$, $X_{3C}$, $X_{4A}$, $X_{4B}$, and $X_{4C}$ is H.

In one aspect, the invention provides a compound of Formula I, Ia, II, or IIa, wherein:
5h) $X_{3A}$ and $X_{4A}$ are each H;
5i) one of $X_{3A}$ and $X_{4A}$ is H and the other of $X_{3A}$ and $X_{4A}$ is F; or
5j) $X_{3A}$ and $X_{4A}$ are each F.

In one aspect, the invention provides a compound of Formula I, Ia, II, or IIa, wherein:
5k) $X_{3B}$ and $X_{4B}$ are each H;
5l) one of $X_{3B}$ and $X_{4B}$ is H and the other of $X_{3B}$ and $X_{4B}$ is F; or
5m) $X_{3B}$ and $X_{4B}$ are each F.

In one aspect, the invention provides a compound of Formula I, Ia, II, or IIa, wherein:
5n) $X_{3C}$ and $X_{4C}$ are each H;
5o) one of $X_{3C}$ and $X_{4C}$ is H and the other of $X_{3C}$ and $X_{4C}$ is F; or
5p) $X_{3C}$ and $X_{4C}$ are each F.

In one aspect, the invention provides a compound of Formula I, Ia, II, or IIa, wherein:
6a) $X_5$ is H;
6b) $X_5$ is F;
6c) $X_5$ is selected from $CF_3$, $CHF_2$, and $CH_2F$;
  6ci) $X_5$ is $CF_3$; or
6d) $X_5$ is selected from $OCF_3$, $OCHF_2$, $OCH_2F$, $OCH_2CF_3$, $OCH_2CHF_2$, and $OCH_2CH_2F$.

In one aspect, the invention provides a compound of Formula I, Ia, II, or IIa, wherein:
7a) z is 0;
7b) z is 1; or
7c) z is 2.

In one aspect, the invention provides a compound of Formula I, Ia, II, or IIa, wherein:

8a)

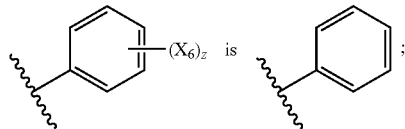 is

8b)

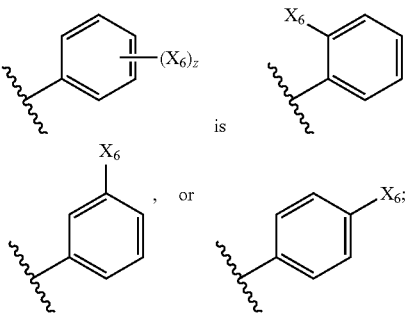

8bi)

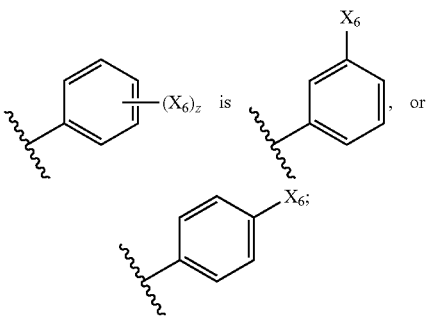

or

8bii)

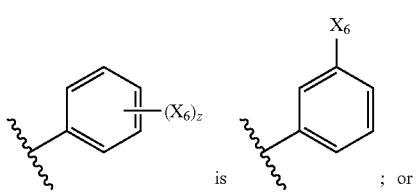; or

8c)

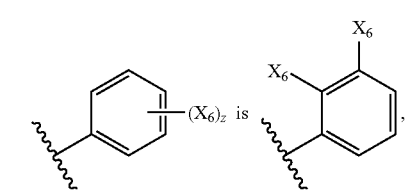,

-continued

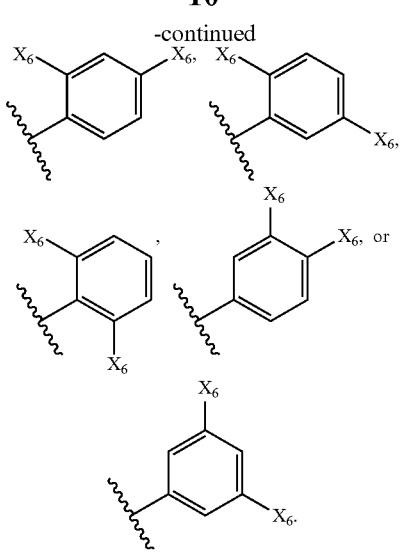

In one aspect, the invention provides a compound of Formula I, Ia, II, or IIa, wherein:
9a) the sum of h+i+j is 3;
9b) the sum of h+i+j≤2;
9c) the sum of h+i+j is 0 or 1;
9d) the sum of h+i+j is 1;
 9di) h is 1, i is 0, and j is 0;
 9dii) h is 0, i is 1, and j is 0; or
 9diii) h is 0, i is 0, and j is 1; or
9e) the sum of h+i+j iso.

In one aspect, the invention provides a compound of Formula I, Ia, II, or IIa, wherein:
10a) the sum of e+f+g≤6;
10b) the sum of e+f+g is 6;
10c) the sum of e+f+g is 5;
10d) the sum of e+f+g is 4;
10e) the sum of e+f+g is 3;
10f) the sum of e+f+g is 2;
 10fi) e is 1, f is 1, and g is 0;
 10fii) e is 1, f is 0, and g is 1;
 10fiii) e is 0, f is 1, and g is 1;
 10fiv) e is 2, f is 0, and g is 0;
 10fv) e is 0, f is 2, and g is 0; or
 10fvi) e is 0, f is 0, and g is 2;
10g) the sum of e+f+g is 1;
 10gi) e is 1, f is 0, and g is 0;
 10gii) e is 0, f is 1, and g is 0; or
 10giii) e is 0, f is 0, and g is 1; or
10h) the sum of e+f+g is 0.

In one aspect, the invention provides a compound of Formula I, Ia, II, or IIa, wherein:
11a) $X_{7A}$, $X_{7B}$, $X_{7C}$, $X_{8A}$, $X_{8B}$, and $X_{8C}$ are each H;
11b) $X_{7A}$, $X_{7B}$, $X_{7C}$, $X_{8A}$, $X_{8B}$, and $X_{8C}$ are each F;
11c) one of $X_{7A}$, $X_{7B}$, $X_{7C}$, $X_{8A}$, $X_{8B}$, and $X_{8C}$ is F and the remaining $X_{7A}$, $X_{7B}$, $X_{7C}$, $X_{8A}$, $X_{8B}$, and $X_{8C}$ are H;
11d) two of $X_{7A}$, $X_{7B}$, $X_{7C}$, $X_{8A}$, $X_{8B}$, and $X_{8C}$ are F and the remaining $X_{7A}$, $X_{7B}$, $X_{7C}$, $X_{8A}$, $X_{8B}$, and $X_{8C}$ are H;
11e) three of $X_{7A}$, $X_{7B}$, $X_{7C}$, $X_{8A}$, $X_{8B}$, and $X_{8C}$ are F and the remaining $X_{7A}$, $X_{7B}$, $X_{7C}$, $X_{8A}$, $X_{8B}$, and $X_{8C}$ are H;
11f) four of $X_{7A}$, $X_{7B}$, $X_{7C}$, $X_{8A}$, $X_{8B}$, and $X_{8C}$ are F and the remaining $X_{7A}$, $X_{7B}$, $X_{7C}$, $X_{8A}$, $X_{8B}$, and $X_{8C}$ are H; or
11g) five of $X_{7A}$, $X_{7B}$, $X_{7C}$, $X_{8A}$, $X_{8B}$, and $X_{8C}$ are F and the remaining $X_{7A}$, $X_{7B}$, $X_{7C}$, $X_{8A}$, $X_{8B}$, and $X_{8C}$ is H.

In one aspect, the invention provides a compound of Formula I, Ia, II, or IIa, wherein:

11h) $X_{7A}$ and $X_{8A}$ are each H;
11i) one of $X_{7A}$ and $X_{8A}$ is H and the other of $X_{7A}$ and $X_{8A}$ is F; or
11j) $X_{7A}$ and $X_{8A}$ are each F.

In one aspect, the invention provides a compound of Formula I, Ia, II, or IIa, wherein:

11k) $X_{7B}$ and $X_{8B}$ are each H;
11l) one of $X_{7B}$ and $X_{8B}$ is H and the other of $X_{7B}$ and $X_{7B}$ is F; or
11m) $X_{7B}$ and $X_{8B}$ are each F.

In one aspect, the invention provides a compound of Formula I, Ia, II, or IIa, wherein:

11n) $X_{7C}$ and $X_{8C}$ are each H;
11o) one of $X_{7C}$ and $X_{8C}$ is H and the other of $X_{7C}$ and $X_{8C}$ is F; or
11p) $X_{7C}$ and $X_{8C}$ are each F.

In one aspect, the invention provides a compound of Formula I, Ia, II, or IIa, wherein:

12a) $X_9$ is H;
12b) $X_9$ is F;
12c) $X_9$ is selected from $CF_3$, $CHF_2$, and $CH_2F$;
12ci) $X_9$ is $CF_3$; or
12d) $X_9$ is selected from $OCF_3$, $OCHF_2$, $OCH_2F$, $OCH_2CF_3$, $OCH_2CHF_2$, and $OCH_2CH_2F$;
12di) $X_9$ is selected from $OCH_2CF_3$, $OCH_2CHF_2$, and $OCH_2CH_2F$; or
12dii) $X_9$ is $OCH_2CF_3$.

In one aspect, the invention provides a compound of Formula I, Ia, II, or IIa, wherein each of the various aspects for each of the Formulae as described herein can be combined in any manner. For example, each of the aspects of $R_1$, $R_2$, $X_1$, $X_2$, $X_5$, $X_6$, $X_9$, e, f, g, h, i, j, v, w, s, t, u, v, w, x, z, $X_{3A}$, $X_{3B}$, $X_{3C}$, $X_{4A}$, $X_{4B}$, $X_{4C}$, $X_{7A}$, $X_{7B}$, $X_{7C}$, $X_{8A}$, $X_{8B}$, and $X_{8C}$ described herein can form various combinations.

In one aspect, the invention provides a compound of Formula I, Ia, II, or IIa, wherein:

13a) the sum of v+w+x is 0; the sum of s+t+u is 0; and $X_5$ is H;
13b) the sum of v+w+x is 0; s is 1; t is 0; u is 0; $X_{3A}$ and $X_{4A}$ are each H; and $X_5$ is H;
13c) the sum of v+w+x is 0; s is 1; t is 0; u is 0; $X_{3A}$ and $X_{4A}$ are each H; and $X_5$ is $CF_3$; or
13d) the sum of v+w+x is 0; s is 1; t is 1; u is 0; $X_{3A}$, $X_{4A}$, $X_{3B}$, and $X_{4B}$ are each H; and $X_5$ is H.

In one aspect, the invention provides a compound of Formula I, Ia, II, or IIa, wherein:

14a) the sum of h+i+j is 0; the sum of e+f+g is 0; and $X_9$ is $OCH_2CF_3$;
14b) the sum of h+i+j is 0; the sum of e+f+g is 0; and $X_9$ is $OCH_2CHF_2$;
14c) the sum of h+i+j is 0; e is 1; f is 0; g is 0; $X_{7A}$ and $X_{8A}$ are each H; and $X_9$ is $CF_3$; or
14d) h is 1; i is 0; j is 0; e is 0; f is 1; g is 1; $X_{7B}$ and $X_{8B}$ are each H; $X_{7C}$ and $X_{8C}$ are each F; and $X_9$ is $CF_3$.

In one aspect, the invention provides a compound of Formula I, Ia, II, or IIa, wherein:

15a) z is 1; the sum of h+i+j is 0; the sum of e+f+g is 0; and $X_9$ is $OCH_2CF_3$;
15b) z is 1; the sum of h+i+j is 0; the sum of e+f+g is 0; and $X_9$ is $OCH_2CHF_2$;
15c) z is 1; the sum of h+i+j is 0; e is 1; f is 0; g is 0; $X_{7A}$ and $X_{8A}$ are each H; and $X_9$ is $CF_3$; or
15d) z is 1; h is 1; i is 0; j is 0; e is 0; f is 1; g is 1; $X_{7B}$ and $X_{8B}$ are each H; $X_{7C}$ and $X_{8C}$ are each F; and $X_9$ is $CF_3$.

In one aspect, the invention provides a compound of Formula I, Ia, II, or IIa, wherein:

16a)

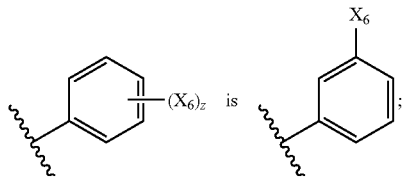

the sum of h+i+j is 0; the sum of e+f+g is 0; and $X_9$ is $OCH_2CF_3$;

16b)

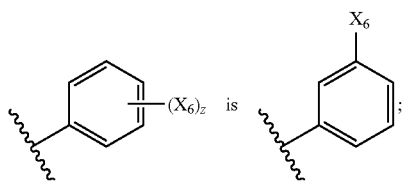

the sum of h+i+j is 0; the sum of e+f+g is 0; and $X_9$ is $OCH_2CHF_2$;

16c)

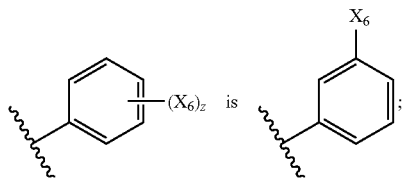

the sum of h+i+j is 0; e is 1; f is 0; g is 0; $X_{7A}$ and $X_{8A}$ are each H; and $X_9$ is $CF_3$; or 16d)

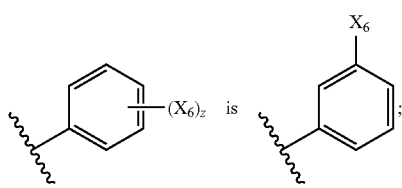

h is 1; i is 0; j is 0; e is 0; f is 1; g is 1; $X_{7B}$ and $X_{8B}$ are each H; $X_{7C}$ and $X_{8C}$ are each F; and $X_9$ is $CF_3$.

It will be understood that the above classes may be combined to form additional preferred classes, as for example the combination of preferred selections for two or more substituents.

The invention provides a compound selected from Table 1.

TABLE 1
| Compound | Chemical Structure |
|---|---|
| 1A | 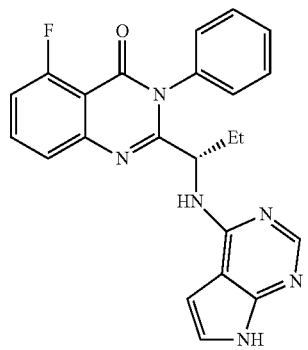 [SMILES: CC[C@H](Nc1ncnc2[nH]ccc12)c1nc2cccc(F)c2c(=O)n1-c1ccccc1] |
| 2A | 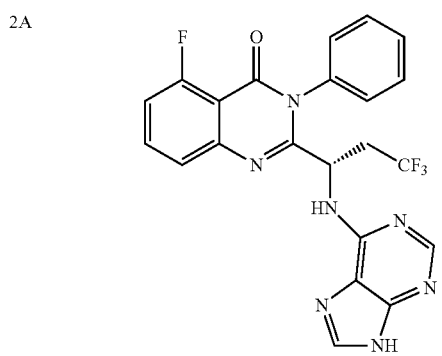 |
| 3A | 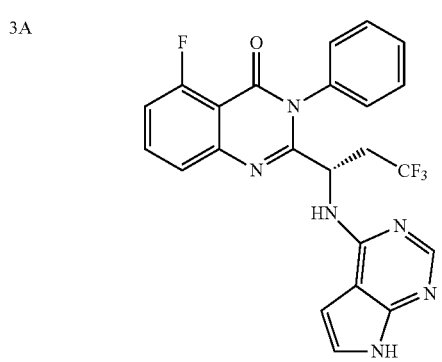 |
| 4A | 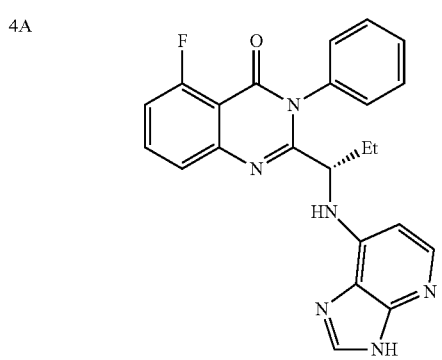 |
TABLE 1-continued
| Compound | Chemical Structure |
|---|---|
| 5A | 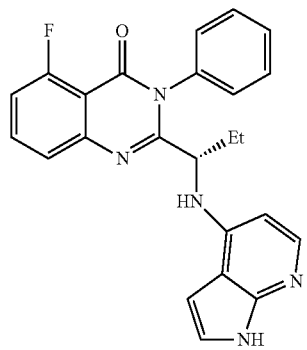 [SMILES: CC[C@H](Nc1ccnc2[nH]ccc12)c1nc2cccc(F)c2c(=O)n1-c1ccccc1] |
| 6A | 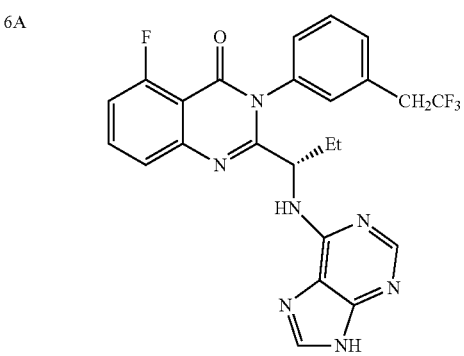 |
| 7A | 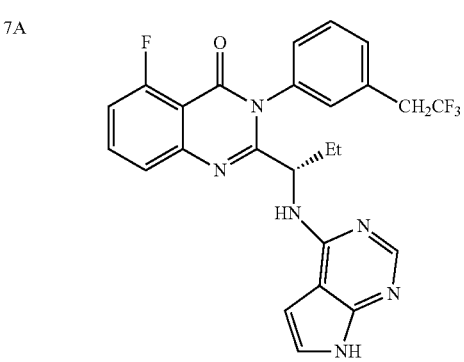 |
| 8A | 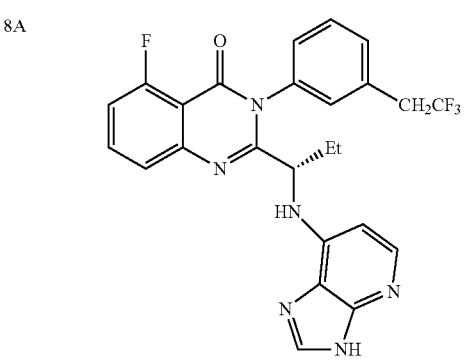 |

TABLE 1-continued

| Compound | Chemical Structure |
|---|---|
| 9A | (5-fluoro-3-(3-(2,2,2-trifluoroethyl)phenyl)quinazolin-4(3H)-one with 2-[(1S)-1-(7H-pyrrolo[2,3-b]pyridin-4-ylamino)propyl] substituent) |
| 10A | (5-fluoro-3-(3-(2,2,2-trifluoroethoxy)phenyl)quinazolin-4(3H)-one with 2-[(1S)-1-(9H-purin-6-ylamino)propyl] substituent) |
| 11A | (5-fluoro-3-(3-(2,2,2-trifluoroethoxy)phenyl)quinazolin-4(3H)-one with 2-[(1S)-1-(7H-pyrrolo[2,3-d]pyrimidin-4-ylamino)propyl] substituent) |
| 12A | (5-fluoro-3-(3-(2,2,2-trifluoroethoxy)phenyl)quinazolin-4(3H)-one with 2-[(1S)-1-(3H-imidazo[4,5-b]pyridin-7-ylamino)propyl] substituent) |
| 13A | (5-fluoro-3-(3-(2,2,2-trifluoroethoxy)phenyl)quinazolin-4(3H)-one with 2-[(1S)-1-(7H-pyrrolo[2,3-b]pyridin-4-ylamino)propyl] substituent) |
| 14A | (5-fluoro-3-(3-(2,2,2-trifluoroethoxy)phenyl)quinazolin-4(3H)-one with 2-[(1S)-1-(7H-pyrrolo[2,3-d]pyrimidin-4-ylamino)ethyl] substituent) |
| 15A | (5-fluoro-3-(4-(2,2,2-trifluoroethoxy)phenyl)quinazolin-4(3H)-one with 2-[(1S)-1-(7H-pyrrolo[2,3-d]pyrimidin-4-ylamino)ethyl] substituent) |
| 16A | (5-fluoro-3-(4-(2,2,2-trifluoroethoxy)phenyl)quinazolin-4(3H)-one with 2-[(1S)-1-(7H-pyrrolo[2,3-d]pyrimidin-4-ylamino)propyl] substituent) |

TABLE 1-continued

| Compound | Chemical Structure |
|---|---|
| 17A | 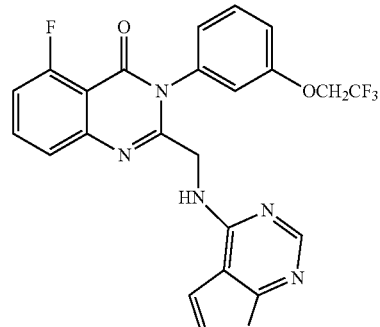 |
| 18A | 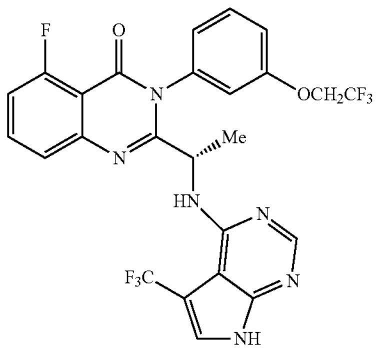 |
| 19A | 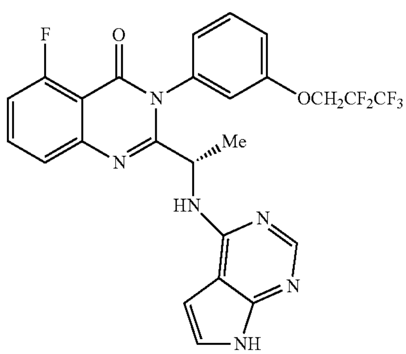 |
| 20A | 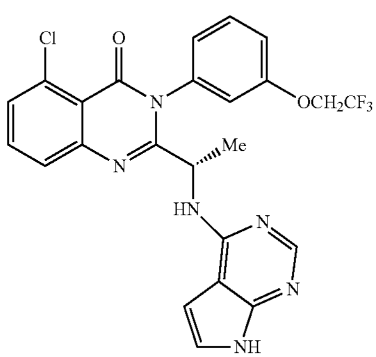 |
| 21A | 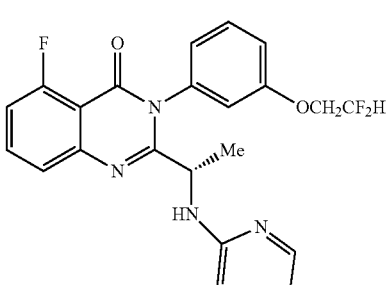 |
| 22A | | or a pharmaceutically acceptable salt or solvate thereof.

In one aspect, a compound of the invention is a pharmaceutically acceptable salt. In one aspect, a compound of the invention is a solvate. In one aspect, a compound of the invention is a hydrate.

The present invention relates to a pharmaceutical composition comprising a compound of the invention as an active ingredient. In one aspect, the invention provides a pharmaceutical composition comprising at least one compound of any of the formulae described herein or a pharmaceutically acceptable salt or solvate thereof, and a pharmaceutically acceptable carrier or excipient. In one aspect, the invention provides a pharmaceutical composition comprising at least one compound of Table 1.

The present invention relates to a method of synthesizing a compound of the invention or a pharmaceutically acceptable salt or solvate thereof. A compound of the invention can be synthesized using a variety of methods known in the art. Scheme 1A and description below depicts a general route for the preparation of a compound of the invention.

Scheme 1A

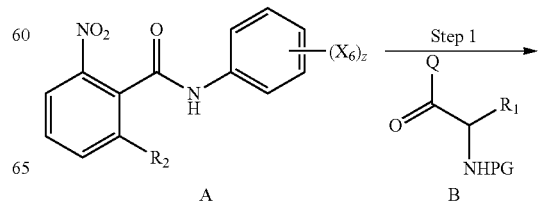

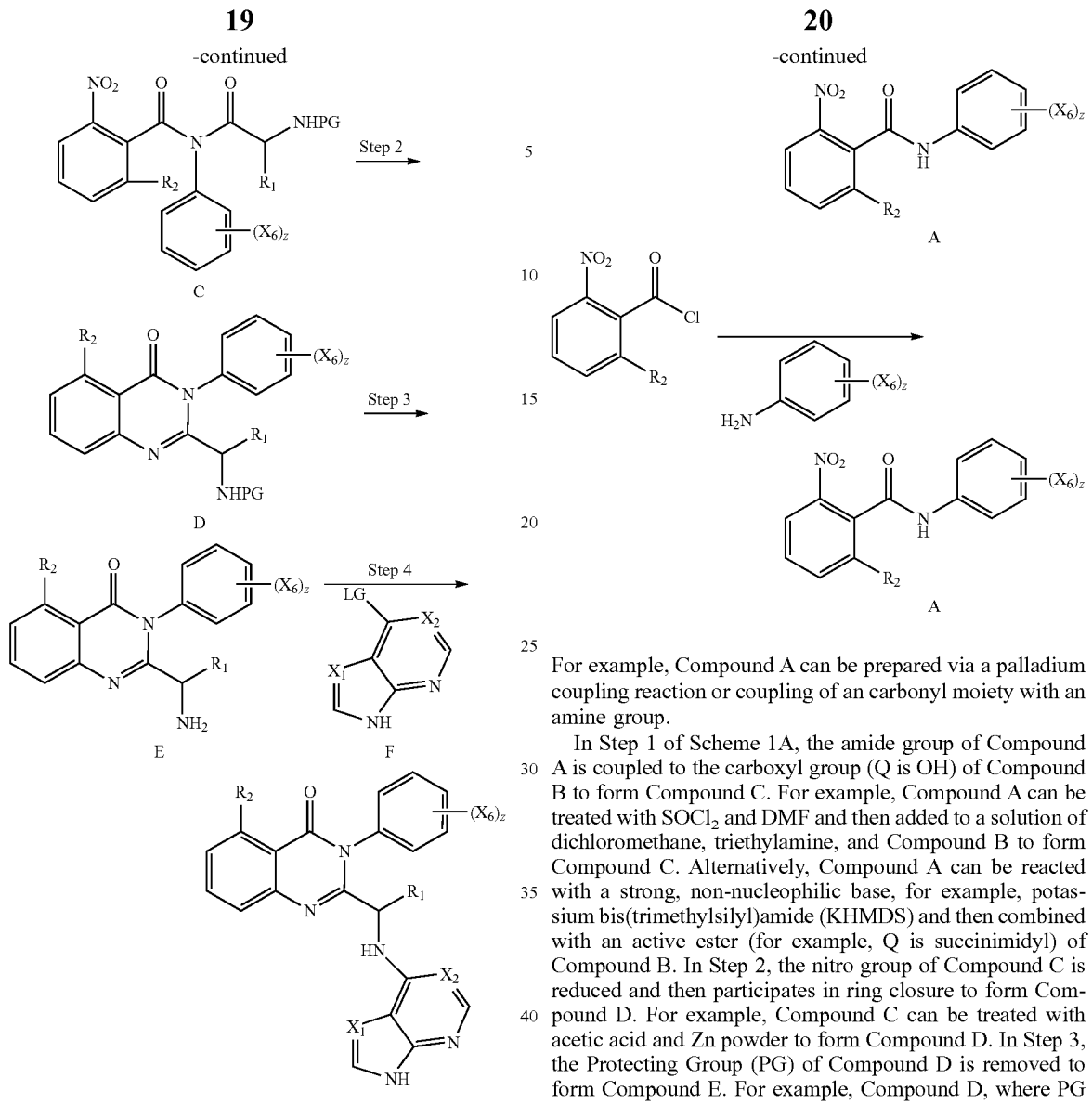

Scheme 1A outlines a preparation for a compound of Formula I. It is understood that Formulae Ia, II, and IIa described herein are subsets of Formula I. Thus, the preparations described for a compound of Formula I can also be applied for the preparation of a compound of any of Formulae Ia, II, and IIa.

The preparation outlined in Scheme 1A begins with Compound A, which is commercially available or is prepared via a one-step reaction from commercially available compounds as shown below:

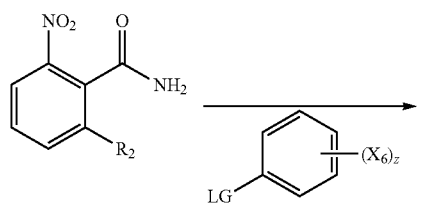

For example, Compound A can be prepared via a palladium coupling reaction or coupling of an carbonyl moiety with an amine group.

In Step 1 of Scheme 1A, the amide group of Compound A is coupled to the carboxyl group (Q is OH) of Compound B to form Compound C. For example, Compound A can be treated with $SOCl_2$ and DMF and then added to a solution of dichloromethane, triethylamine, and Compound B to form Compound C. Alternatively, Compound A can be reacted with a strong, non-nucleophilic base, for example, potassium bis(trimethylsilyl)amide (KHMDS) and then combined with an active ester (for example, Q is succinimidyl) of Compound B. In Step 2, the nitro group of Compound C is reduced and then participates in ring closure to form Compound D. For example, Compound C can be treated with acetic acid and Zn powder to form Compound D. In Step 3, the Protecting Group (PG) of Compound D is removed to form Compound E. For example, Compound D, where PG is tert-butyloxycarbonyl (BOC), can be treated with dichloromethane and trifluoroacetic acid to form Compound E. In Step 4, the amino group of Compound E is coupled to Compound F to provide a compound of Formula I. For example, a solution of Compound E in t-BuOH can be treated with diisopropylethylamine and compound F, where Leaving Group (LG) is a halogen atom, to provide a compound of Formula I.

The present invention also comprehends deuterium labeled compounds, which are identical to those recited in any of the formulae described herein and the compounds listed in Table 1 but for the fact that one or more hydrogen atoms is replaced by a deuterium atom having an abundance of deuterium at that position that is substantially greater than the natural abundance of deuterium, which is 0.015%.

The term "deuterium enrichment factor" as used herein means the ratio between the deuterium abundance and the natural abundance of a deuterium. In one aspect, a compound of the invention has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

A compound of the invention or a pharmaceutically acceptable salt or solvate thereof that contains the aforementioned deuterium atom(s) is within the scope of the invention. Further, substitution with heavier deuterium, i.e., $^2$H, can afford certain therapeutic advantages resulting from greater metabolic stability, for example, increased in vivo half-life or reduced dosage requirements.

The present invention relates to a method of synthesizing a deuterium labeled compound of the invention or a pharmaceutically acceptable salt or solvate thereof.

The deuterium labeled compounds of the invention can be prepared using any of a variety of art-recognized techniques. For example, deuterium labeled compounds of the invention can generally be prepared by carrying out the procedures disclosed in Scheme 1A and the description provided herein for the preparation of a compound of Formula I. For example, a deuterium labeled compound can be prepared by starting with deuterium labeled Compound A and/or substituting a readily available deuterium labeled reagent for a non-deuterium labeled reagent.

Methods of Use

The invention also provides methods of using a compound or pharmaceutical composition of the invention to treat or prevent disease conditions, including but not limited to diseases and disorders mediated by activity of one or more types of PI3 kinase. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3Ks play a key role in intracellular trafficking through the synthesis of PIP3 and PIP2. The PIKKs are protein kinases that control cell growth (mTORC1) or monitor genomic integrity (ATM, ATR, DNA-PK, and hSmg-1).

In one aspect, the invention provides a compound that selectively inhibits the activity of PI3Kδ isoform while having a relatively low inhibitory potency against the other PI3K isoforms. For example, a compound of the invention inhibits the activity of PI3Kδ with a potency at least 2-fold, 5-fold, 10-fold, 20-fold, 30-fold, 50-fold, 100-fold, 500-fold, or 1000-fold the potency with which the compound inhibits other PI3K isoforms, such as PI3Kα, PI3Kβ, and PI3Kγ, as measured by assays commonly utilized in the art.

The invention further provides methods of inhibiting PI3Kδ activity, including methods of selectively modulating the activity of the PI3Kδ isozyme in cells, especially leukocytes, osteoclasts, and cancer cells.

Of particular benefit are methods of selectively modulating PI3Kδ activity in the clinical setting in order to ameliorate diseases or disorders mediated by PI3Kδ activity. Diseases or disorders characterized by excessive or inappropriate PI3Kδ activity can be treated through use of selective modulators of PI3Kδ according to the invention.

Moreover, the invention provides a pharmaceutical composition comprising a selective PI3Kδ inhibitor. Also provided are articles of manufacture comprising a selective PI3Kδ inhibitor compound (or a pharmaceutical composition comprising the compound) and instructions for using the compound.

In one aspect, the methods described herein benefit from the use of a compound that selectively inhibits the activity of PI3Kδ. The term "selective PI3Kδ inhibitor" as used herein refers to a compound that inhibits the PI3Kδ isozyme more effectively (e.g., at least twice, 5 times, 10 times, 20 times, 30 times, 50 times, 100 times, 500 times, or 1000 times more effective) than other isozymes of the PI3K family.

The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$." $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

In one aspect, the invention provides a compound that selectively inhibits the activity of PI3Kδ isoform with $IC_{50}$ lower than $5 \times 10^{-6}$ M, $4 \times 10^{-6}$ M, $3 \times 10^{-6}$ M, $2.5 \times 10^{-6}$ M, $2.0 \times 10^{-6}$ M, $1.5 \times 10^{-6}$ M, $1.0 \times 10^{-6}$ M, $0.5 \times 10^{-6}$ M, $0.3 \times 10^{-6}$ M, $0.2 \times 10^{-6}$ M, $0.15 \times 10^{-6}$ M, or $0.1 \times 10^{-6}$ M in a lipid kinase assay using the Homogeneous Time Resolved Fluorescence (HTRF) format.

In one aspect, the invention provides a compound that selectively inhibits the activity of PI3Kγ isoform with $IC_{50}$ lower than $10 \times 10^{-6}$ M, $9 \times 10^{-6}$ M, $8 \times 10^{-6}$ M, $7 \times 10^{-6}$ M, $6 \times 10^{-6}$ M, $5 \times 10^{-6}$ M, $4 \times 10^{-6}$ M, $3 \times 10^{-6}$ M, $2 \times 10^{-6}$ M, $1.5 \times 10^{-6}$ M in a lipid kinase assay using the HTRF format. In one aspect, the invention provides a compound that selectively inhibits the activity of PI3Kγ isoform with $IC_{50}$ higher than $0.01 \times 10^{-6}$ M, $0.05 \times 10^{-6}$ M, $0.1 \times 10^{-6}$ M, $0.15 \times 10^{-6}$ M, $0.2 \times 10^{-6}$ M, $0.25 \ 10^{-6}$ M, or $0.3 \times 10^{-6}$ M in a lipid kinase assay using the HTRF format.

In one aspect, the invention provides a compound that selectively inhibits the activity of PI3Kα isoform with $IC_{50}$ lower than $150 \times 10^{-6}$ M, $120 \times 10^{-6}$ M, $100 \times 10^{-6}$ M, $50 \times 10^{-6}$ M, $40 \times 10^{-6}$ M, $30 \times 10^{-6}$ M, or $20 \times 10^{-6}$ M in a lipid kinase assay using the HTRF format. In one aspect, the invention provides a compound that selectively inhibits the activity of PI3Kα isoform with $IC_{50}$ higher than $0.1 \times 10^{-6}$ M, $0.5 \times 10^{-6}$ M, $1 \times 10^{-6}$ M, $2 \times 10^{-6}$ M, $3 \times 10^{-6}$ M, $4 \times 10^{-6}$ M, or $5 \times 10^{-6}$ M in a lipid kinase assay using the HTRF format.

In one aspect, the invention provides a compound that selectively inhibits the activity of PI3Kβ isoform with $IC_{50}$ lower than $50 \times 10^{-6}$ M, $40 \times 10^{-6}$ M, $30 \times 10^{-6}$ M, $20 \times 10^{-6}$ M, $15 \times 10^{-6}$ M, or $10 \times 10^{-6}$ M in a lipid kinase assay using the HTRF format. In one aspect, the invention provides a compound that selectively inhibits the activity of PI3Kβ isoform with $IC_{50}$ higher than $0.1 \times 10^{-6}$ M, $0.5 \times 10^{-6}$ M, $1 \times 10^{-6}$ M, $2 \times 10^{-6}$ M, $3 \times 10^{-6}$ M, $4 \times 10^{-6}$ M, or $5 \times 10^{-6}$ M in a lipid kinase assay using the HTRF format.

Accordingly, a "selective PI3Kδ inhibitor" alternatively can be understood to refer to a compound that exhibits a 50% inhibitory concentration ($IC_{50}$) with respect to PI3Kδ that is at least at least 10-fold, preferably at least 20-fold, and more preferably at least 30-fold, lower than the $IC_{50}$ value with respect to any or all of the other Class I PI3K family members.

The methods provided herein comprise administering to the subject a therapeutically effective amount of a compound of the invention for the treatment or prevention of a disease or disorder (e.g., a disease or disorder mediated by activity of one or more types of PI3 kinase, such as PI3Kδ).

Inflammatory and Autoimmune Disease

The invention provides a method for treating or preventing an inflammatory or autoimmune disorder in a subject comprising administering to the subject in need thereof an effective amount of a compound of the invention. In one aspect, the invention provides a method of treating or preventing an inflammatory disorder.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke immune response to foreign antigen, and autoimmune responses. Accordingly, inflammatory disorders amenable to the invention encompass disorders associated with reactions of the specific defense system as well as with reactions of the nonspecific defense system.

As used herein, the term "specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

In one aspect, the invention provides a method of treating or preventing an autoimmune disease.

"Autoimmune disease" as used herein refers to any group of disorders in which tissue injury is associated with humoral or cell-mediated responses to the body's own constituents. "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia.

The methods of the invention include methods for the treatment or prevention of disorders associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

In one aspect, a compound of the invention inhibits superoxide release by neutrophils. Superoxide is released by neutrophils in response to any of a variety of stimuli, including signals of infection, as a mechanism of cell killing. For example, superoxide release is known to be induced by tumor necrosis factor alpha (TNFα), which is released by macrophages, mast cells, and lymphocytes upon contact with bacterial cell wall components such as lipopolysaccharide (LPS). TNFα is an extraordinarily potent and promiscuous activator of inflammatory processes, being involved in activation of neutrophils and various other cell types, induction of leukocyte/endothelial cell adhesion, pyrexia, enhanced MHC class I production, and stimulation of angiogenesis. Alternatively, superoxide release can be stimulated by formyl-Met-Leu-Phe (fMLP) or other peptides blocked at the N-terminus by formylated methionine. Such peptides are not normally found in eukaryotes, but are fundamentally characteristic of bacteria, and signal the presence of bacteria to the immune system. Leukocytes expressing the fMLP receptor, e.g., neutrophils and macrophages, are stimulated to migrate up gradients of these peptides (i.e., chemotaxis) toward loci of infection. In one aspect, a compound of the invention inhibits stimulated, superoxide release by neutrophils in response to either TNFα or fMLP. Other functions of neutrophils, including stimulated exocytosis and directed chemotactic migration, also can be inhibited by the PI3Kδ inhibitors of the invention. Accordingly, a compound of the invention is useful in treating disorders, such as inflammatory disorders, that are mediated by any or all of these neutrophil functions.

The invention enables methods of treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroidassociated ophthalmopathy; ecsinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vascuiitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjðgren's syndrome; diseases involving, leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; cytokine-induced toxicity' acute disseminated encephalomyelitis (ADEM), Addison's disease; antiphospholipid antibody syndrome (APS); oemphigus; and passive cutaneous analyphylaxis.

In one aspect, one of more of the subject methods are effective in ameliorating symptoms associated with rheumatoid arthritis including but not limited to a reduction in the swelling of joints (e.g., ankle, knee), a reduction in serum anti-collagen levels, and/or a reduction in joint pathology such as bone resorption, cartilage damage, pannus, and/or inflammation.

Respiratory Disease

The invention provides a method for treating or preventing a respiratory disease in a subject comprising administering to the subject in need thereof an effective amount of a compound of the invention. Respiratory diseases include but are not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another aspect, a compound of the invention is used for the treatment of asthma. Also, a compound of the invention may be used for the treatment of endotoxemia and sepsis. In one embodiment, a compound of the invention is used for the treatment of rheumatoid arthritis (RA). In yet another embodiment, a compound of the invention is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

Hyperproliferative Disorder

The invention provides a method for treating or preventing a hyperaproliferative disorder in a subject comprising administering to the subject in need thereof an effective amount of a compound of the invention.

The invention includes methods of using a compound of the invention to inhibit the growth or proliferation of cancer cells of hematopoietic origin, cancer cells of lymphoid origin, and more preferably cancer cells related to or derived from B lymphocytes or B lymphocyte progenitors. Cancers amenable to treatment using the method of the invention include, without limitation, lymphomas, e.g., malignant neoplasms of lymphoid and reticuloendothelial tissues, such as Burkitt's lymphoma, Hodgkin's lymphoma, non-Hodgkin's lymphomas, lymphocytic lymphomas and the like; multiple myelomas; as well as leukemias such as lymphocytic leukemias, chronic myeloid (myelogenous) leukemias, and the like. In one embodiment, a compound of the invention can be used to inhibit or control the growth or proliferation of chronic myeloid (myelogenous) leukemia cells. Cancer may include acute myeloid leukemia, *thymus*, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g., Lymphoma and Kaposi's Sarcoma) or viral-induced cancer. In some embodiments, the method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method of treating diseases related to vasculogenesis or angiogenesis in a subject that comprises administering to said subject a therapeutically effective amount of a compound of the invention or a pharmaceutically acceptable salt or solvate thereof.

Cardiovascular Disease

The invention provides a method for treating or preventing a cardiovascular disease in a subject comprising administering to the subject in need thereof an effective amount of a compound of the invention. Examples of cardiovascular conditions include, but are not so limited to, atherosclerosis, restenosis, vascular occlusion, and carotid obstructive disease.

In addition, a compound of the invention may be used for the treatment of arteriosclerosis, including atherosclerosis. Arteriosclerosis is a general term describing any hardening of medium or large arteries. Atherosclerosis is a hardening of an artery specifically due to an atheromatous plaque.

Disease of the Bone

The invention provides a method for treating or preventing a disease of the bone in a subject comprising administering to the subject in need thereof an effective amount of a compound of the invention. In one aspect, the disease of the bone is a disease in which osteoclast function is abnormal or undesirable. A compound of the invention can be of value in treating osteoporosis, Paget's disease, and related bone resorption disorders.

Reperfusion Injury

The invention provides a method for treating or preventing a reperfusion injury in a subject comprising administering to the subject in need thereof an effective amount of a compound of the invention. The method can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of PI3Kδ activity will result in reduced amounts of reperfusion injury in such situations.

With respect to the nervous system, global ischemia occurs when blood flow to the entire brain ceases for a period. Global ischemia can result from cardiac arrest. Focal ischemia occurs when a portion of the brain is deprived of its normal blood supply. Focal ischemia can result from thromboembolytic occlusion of a cerebral vessel, traumatic head injury, edema, or brain tumor. Even if transient, both global and focal ischemia can cause widespread neuronal damage. Although nerve tissue damage occurs over hours or even days following the onset of ischemia, some permanent nerve, tissue damage can develop in the, initial minutes following the cessation of blood flow to the brain.

Ischemia also can occur in the heart in myocardial infarction and other cardiovascular disorders in which the coronary arteries have been obstructed as a result of atherosclerosis, thrombus, or spasm. Accordingly, the invention is believed to be useful for treating cardiac tissue damage, particularly damage resulting from cardiac ischemia or caused by reperfusion injury in subjects.

Central Nervous System (CNS) Disorders

The invention provides a method for treating or preventing a CNS disorder in a subject comprising administering to the subject in need thereof an effective amount of a compound of the invention. In one aspect, the CNS disorder is schizophrenia, psychosis, or a cognitive disorder. The methods disclosed herein are suitable for alleviating one or more symptoms of a variety of CNS disorders. Individuals with a CNS disorder frequently exhibit one or more symptoms that are characteristic of the particular disorder. It is also contemplated that a constellation of symptoms from multiple CNS disorders in the same individual can be alleviated by the present methods. In this regard, recognizing symptoms from CNS disorders, and determining alleviation of the symptoms during or after practice of the present method is well within the purview of a person having ordinary skill in the art and can be performed using any suitable clinical, diagnostic, observational, or other techniques. For example, symptoms of schizophrenia include but are not limited to delusions, hallucinations, disorganized speech, catatonic behavior, cognitive symptoms, or a combination thereof. Symptoms of psychosis include delusions, hallucinations, or a combination thereof. A reduction in any of these particular symptoms resulting from practicing the methods disclosed herein is considered an alleviation of the symptom. Particular CNS disorders presenting symptoms suitable for alleviation by the present methods include but are not limited to: broad spectrum psychosis such as bipolar disorders; depression; mood disorders; anxiety; obsessive compulsive disorders; sleep disorders; feeding disorders such as anorexia and bulimia; panic attacks; drug addictions and withdrawal from drug addictions; attention deficit disorders; cognitive disorders; age-associated memory impairment (AAMI); neurodegenerative disorders such as Alzheimer's disease, Parkinson's disease, and stroke related dementia; Down's Syndrome; and combinations thereof. Symptoms of each of these disorders are well known. Recognizing and determining a reduction in the symptoms of any of these particular disorders can be readily performed by those skilled in the art. In specific embodiments, the CNS disorder is schizophrenia, psychosis or a cognitive disorder.

Other Diseases

Additionally, the compounds of the invention may be used for the treatment of bursitis, lupus, acne, aplastic anemia, autoimmume hepatitis, coeliac disease, Crohn's disease, diabetes mellitus (type 1), Goodpasture's syndrome, Graves' disease, Guillain-barre syndrome (GBS), Hashimoto's disease, inflammatory bowel disease, liver disease, lupus erythematosus, myasthenia gravis, opsoclonus myoclonus syndrome (OMS), optic neuritis, Ord's thyroiditis, ostheoarthritis, uveoretinitis, pemphigus, polyarthritis, primary biliary cirrhosis, Reiter's syndrome, Takayasu's arteritis, temporal arteritis, warm autoimmune hemolytic anemia, Wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, panaocreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

Patients that can be treated with a compound of the invention or a pharmaceutically acceptable salt or solvate thereof, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer;

cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myelocloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer, thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HYV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Mullerian tumor, oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; *thymus* cancer such as to thymomas, thymic carcinomas, Hodgkin disease, non-Hodgkin lymphomas carcinoids or carcinoid tumors; rectal cancer; and colon cancer. A compound of the invention may be useful for the prevention of blastocyte implantation in a subject.

Combination Treatment

The invention also provides methods for combination therapies in which a therapeutic agent known to modulate other pathways, or other components of the same pathway, or even overlapping sets of target enzymes are used in combination with a compound of the invention or a pharmaceutically acceptable salt or a solvate thereof.

In one aspect, a compound of the invention may present synergistic or additive efficacy when administered in combination with therapeutic agents that inhibit IgE production or activity. Such combination can reduce the undesired effect of high level of IgE associated with the use of one or more PI3Kδ inhibitors, if such effect occurs. This may be particularly useful in treatment of autoimmune and inflammatory disorders (AIID) such as rheumatoid arthritis. Additionally, the administration of a compound of the invention in combination with inhibitors of mTOR may also exhibit synergy through enhanced inhibition of the PI3K pathway.

Therapeutic agents that inhibit IgE production are known in the art and they include but are not limited to one or more of TEI-9874, 2-(4-(6-cyclohexyloxy-2-naphthyloxy)phenylacetamide)benzoic acid, rapamycin, rapamycin analogs (i.e., rapalogs), TORC1 inhibitors, TORC2 inhibitors, and any other compounds that inhibit mTORC1 and mTORC2. Therapeutic agents that inhibit IgE activity include, for example, anti-IgE antibodies such as for example Omalizumab and TNX-901.

For treatment of autoimmune diseases, a compound of the invention can be used in combination with commonly prescribed drugs including but not limited to Enbrel®, Remicade®, Humira®, Avonex®, and Rebil®. For treatment of respiratory diseases, the subject compounds or pharmaceutical compositions can be administered in combination with commonly prescribed drugs including but not limited to Xolair®, Advair®, Singulair®, and Spiriva®.

A compound of the invention may be formulated or administered in conjunction with other therapeutic agents that act to relieve the symptoms of inflammatory conditions such as encephalomyelitis, asthma, and the other diseases described herein. These therapeutic agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen®) or hydroxychloroquine (Plaquenil®) may also be very useful in some individuals with lupus. They are most often prescribed for skin and joint symptoms of lupus. Azathioprine (Imuran®) and cyclophosphamide (Cytoxan®); suppress inflammation and tend to suppress the immune system. Other therapeutic agents, e.g., methotrexate and cyclosporin are used to control the symptoms of lupus. Anticoagulants are employed to prevent blood from clotting rapidly. They range from aspirin at very low dose which prevents platelets from sticking, to heparin/Coumadin®.

In another one aspect, this invention also relates to inhibiting abnormal cell growth in a subject with a therapy comprising a compound of the invention or a pharmaceutically acceptable salt or solvate thereof, in combination with an amount of an anti-cancer agent (e.g., a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as GLEEVEC® (Imatinib Mesylate), VELCADE® (bortezomib), CASODEX® (bicalutamide), IRESSA™ (gefitinib), and Adriamycin® as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, inelphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, CASODEX®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston®); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; XELODA®; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, AVASTIN®, ERBITUX®, RITUXAN®, TAXOL™, ARIMIDEX®, TAXOTERE™, and VELCADE®.

This invention further relates to a method for using a compound of the invention in combination with radiation therapy in inhibiting abnormal cell growth or treating the hyperproliferative disorder in the subject. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, a compound of the invention can render abnormal cells more sensitive to treatment with radiation for purposes of killing and/or inhibiting the growth of such cells. Accordingly, this invention further relates to a method for sensitizing abnormal cells in a subject to treatment with radiation which comprises administering to the subject an amount of a compound of the present invention or pharmaceutically acceptable salt or solvate thereof, which amount is effective is sensitizing abnormal cells to treatment with radiation. The amount of the compound or pharmaceutically acceptable salt or solvate thereof in this method can be determined according to the means for ascertaining effective amounts of such compounds described herein.

A compound of the invention can be used in combination with an amount of one or more therapeutic agents selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metallo-proteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998). WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional 5 Application No. 60/148,464 (filed Aug. 12, 1999), U.S. Pat. No. 5,863,949 (issued Jan. 26, 1999) U.S. Pat. No. 5,861,510

(issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix metalloproteinases (i.e., MAP-1, MMP-3, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of treating or preventing a cardiovascular disease in a subject which comprises an amount of a compound of the invention or a pharmaceutically acceptable salt or solvate thereof, or an isotopically-labeled derivative thereof, and an amount of one or more therapeutic agents use for the treatment of cardiovascular diseases.

Examples for use in a combination therapy for cardiovascular disease applications are anti-thrombotic agents, e.g., prostacyclin and salicylates, thrombolytic agents, e.g., streptokinase, urokinase, tissue plasminogen activator (TPA) and anisoylated plasminogenstreptokinase activator complex (APSAC), anti-platelet agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

Therapeutic agents which may be administered in conjunction with a compound of the invention include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-2-(2-pyridinylethoxy]hexyl]-amino]methyl]benzenemethanol; diuretics, e.g., amiloride; anticholinergics, e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments may be used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and B, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-FIT, serotonin) receptor agonists and antagonists.

Therapeutic agents for use in a combination can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobac-*

*terium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the therapeutic agents disclosed herein or other suitable agents, depending on the condition being treated. Hence, in some embodiments the compounds of the invention will be co-administered with other agents as described above. When used in combination therapy, the compounds described herein may be administered with the second therapeutic agent simultaneously or separately. This administration in combination can include simultaneous administration of the two therapeutic agents in the same dosage form, simultaneous administration in separate dosage forms, and separate administration. That is, a compound described herein and any of the therapeutic agents described above can be formulated together in the same dosage form and administered simultaneously. Alternatively, a compound of the present invention and any of the therapeutic agents described above can be simultaneously administered, wherein both the agents are present in separate formulations. In another alternative, a compound of the present invention can be administered just followed by and any of the agents described above, or vice versa. In the separate administration protocol, a compound of the present invention and any of the therapeutic agents described above may be administered a few minutes apart, or a few hours apart, or a few days apart.

Pharmaceutical Compositions

The invention provides a pharmaceutical composition comprising a compound of the invention or a pharmaceutically acceptable salt of solvate thereof, and a pharmaceutical carrier, diluent, or excipient. The pharmaceutical composition of the invention is useful in any of the methods of use described herein.

The subject pharmaceutical compositions are typically formulated to provide a therapeutically effective amount of a compound of the present invention as the active ingredient, or a pharmaceutically acceptable salt or solvate thereof. Where desired, the pharmaceutical compositions contain a pharmaceutically acceptable salt or solvate, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

In some embodiments, the concentration of one or more of the compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds of the present invention is in the range of 0.0001-10 g, 0.0005-9 g, 0.001-8 g, 0.005-7 g, 0.01-6 g, 0.05-5 g, 10 0.1-4 g, 0.5-4 g, or 1-3 g.

Described below are non-limiting exemplary pharmaceutical compositions and methods for preparing the same.

In some embodiments, the invention provides a pharmaceutical composition for oral administration containing a compound of the invention and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or nonaqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyloleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB (Hydrophilic-lipophilic balance) value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysaphospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylesters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl camitines, palmitoyl camitines, myristoyl camitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, to sucrose monostearate, sucrose monolaurate, sucrose mono-palmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, .epsilon.-caprolactam, N-alkyl-1pyrrolidone, N-hydroxyalkylpyrrolidone, N-alkylpiperidone, N-alkylcaprolactam, dimethylacetamide and polyvinylpyrrolidone; esters such as ethyl propionate, tributyl citrate, acetyl triethylcitrate, acetyl tributyl citrate, triethylcitrate, ethyloleate, ethyl caprylate, ethyl butyrate, triacetin, propylene glycol monoacetate, propylene glycol diacetate, $\epsilon$-caprolactone and isomers thereof, $\delta$-valerolactone and isomers thereof, $\beta$-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium ahuninum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenyl sulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

In some embodiments, the invention provides a pharmaceutical composition for transdermal delivery containing a compound of the present invention and a pharmaceutical excipient suitable for transdermal delivery.

Methods are further provided for administering a compound of the invention via eye drop, intraocular injection, intravitreal injection, topically, or through the use of a drug eluting device, microcapsule, implant, or microfluidic device. In some cases, a compound of the invention is administered with a carrier or excipient that increases the intraocular penetrance of the compound such as an oil and water emulsion with colloid particles having an oily core surrounded by an interfacial film.

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quaternary ammonium compound, a cationic lipid, an amino alcohol, a biguanidine salt, a cationic compound or a mixture thereof. In some cases the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, myristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising polyoxyl-40 hydrogenated castor oil, polyoxyl hydrogenated castor oil or polyoxyl-100 hydrogenated castor oil.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art.

See, e.g., U.S. Pat. Nos. 5,023,252, 4,992,445 and 5,001,139. Such patches may be constructed for continuous, pulsatile, or on demand delivery of pharmaceutical agents.

Compositions for inhalation or insulation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., *Principles of Drug Action*, Third Edition, Churchill Livingston, N. Y., 1990; Katzung, ed., *Basic and Clinical Pharmacology*, Ninth Edition, McGraw Hill, 20037ybg; Goodman and Gilman, eds., The Pharmacological Basis of Therapeutics, Tenth Edition, McGraw Hill, 2001; *Remington Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Compounds can also be administered intraadiposally or intrathecally.

The compounds of the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, and the body weight of the subject to be treated.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day. In one aspect, from about 1 to about 50 mg per day, and from about 5 to about 40 mg per day are examples of dosages that may be used. An exemplary dosage is from about 10 to about 30 mg per day, from about 0.05 to about 2.5 g/day. In some instances, dosage levels below the lower limit of the aforesaid range may be more than adequate, while in other cases still larger doses may be employed without causing any harmful side effect, e.g., by dividing such larger doses into several small doses for administration throughout the day.

In one aspect, administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 2, 3, 4, 5, or 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures so such as balloon angioplasty. Without being bound by theory, a compound of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester)copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds.

A compound of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, a compound of the invention may be covalently linked to a stent or graft. A covalent linker may be used which degrades in vivo, leading to the release of the compound of the invention. Any bio-labile linkage may be used for such a purpose, such as ester, amide or anhydride linkages. A compound of the invention may additionally be administered intravascularly from a balloon used during angioplasty. Extravascular administration of a compound via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream, for rectal administration as a suppository, or for inhalation as a volatilized aqueous suspension or small particle suspension. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

The activity of a compound of the invention may be determined by the following procedure, known in the art and by the procedure described in the examples below.

The following Examples are illustrative and should not be interpreted in any way so as to limit the scope of the invention.

EXAMPLES

Example 1

Experimental Procedures and Compound Characterization

Example 1A

Synthesis of (S)-2-(1-((7H-pyrrolo[2,3-d]pyrimidin-4-yl)amino)propyl)-5-fluoro-3-phenylquinazolin-4(3H)-one (Compound 1A)

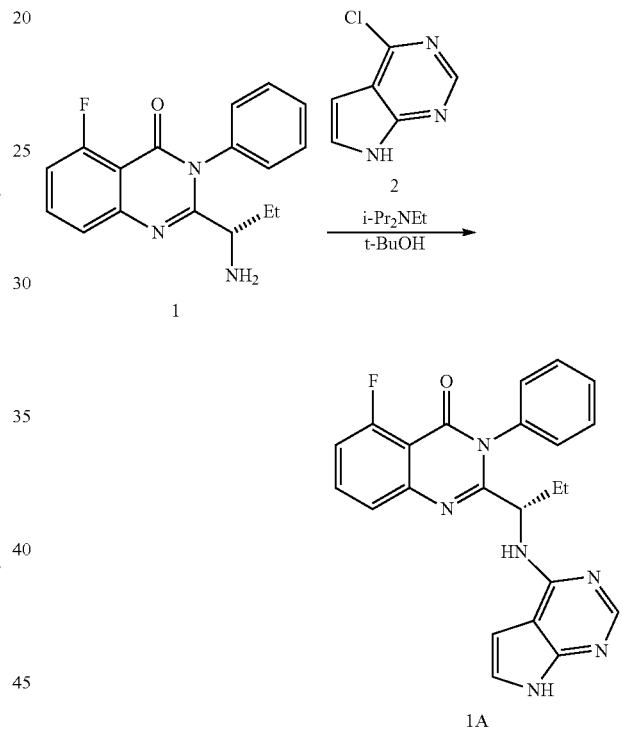

Under nitrogen, to (S)-2-(1-aminopropyl)-5-fluoro-3-phenylquinazolin-4(3H)-one (1) (27 mg, 0.091 mmol, 1.0 equiv) in t-BuOH (0.5 mL) at 23° C. was added 4-chloro-7H-pyrrolo[2,3-d]pyrimidine (2) (21 mg, 0.14 mmol, 1.5 equiv) and diisopropylethylamine (63 µL, 0.36 mmol, 4.0 equiv). After stirring for 16 hr at 120° C. in a sealed tube, the reaction mixture was concentrated in vacuo and the residue was purified by preparative TLC eluting with CH$_2$Cl$_2$/MeOH to afford 12 mg of compound 1A, as a colorless solid (32%).

NMR Spectroscopy: $^1$H NMR (400 MHz, CD$_3$OD, 23° C., δ): 8.00 (s, 1H), 7.80-7.70 (m, 1H), 7.61-7.38 (m, 6H), 7.16 (dd, J=10.8 Hz, 8.0 Hz, 1H), 7.06 (d, J=3.2 Hz, 1H), 6.62 (d, J=3.2 Hz, 1H), 4.91-4.84 (m, 1H), 2.16-2.00 (m, 1H), 1.97-1.81 (m, 1H), 0.88 (t, J=7.5 Hz, 3H). $^{19}$F NMR (375 MHz, CD$_3$OD, 23° C., δ): −112.4 (s, 1F).

Example 1B

Synthesis of (S)-2-(1-((9H-purin-6-yl)amino)-3,3,3-trifluoropropyl)-5-fluoro-3-phenylquinazolin-4(3H)-one (Compound 2A)

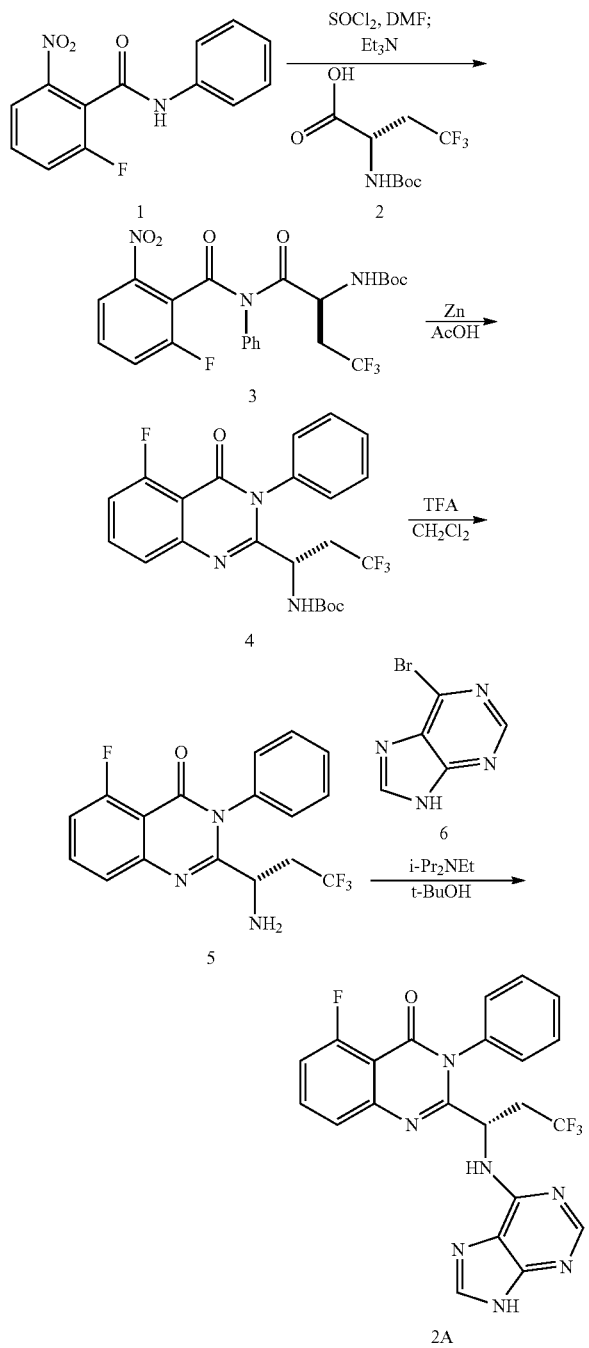

(S)-tert-butyl (4,4,4-trifluoro-1-(2-fluoro-6-nitro-N-phenylbenzamido)-1-oxobutan-2-yl)carbamate (3)

Under nitrogen, to 2-fluoro-6-nitro-N-phenylbenzamide (1) (406 mg, 1.56 mmol, 1.00 equiv) in SOCl$_2$ (0.57 mL) at 23° C. was added DMF (4.9 μL, 0.062 mmol, 4.0 mol %). After stirring for 5 hr at 85° C., the reaction mixture was concentrated in vacuo. The residue was dissolved in CH$_2$Cl$_2$ (2 mL) and was added to a solution of (S)-2-((tert-butoxycarbonyl)amino)-4,4,4-trifluorobutanoic acid (2) (400 mg, 1.56 mmol, 1.00 equiv) and triethylamine (217 μL, 1.56 mmol, 1.00 equiv) in CH$_2$Cl$_2$ (3 mL) at 0° C. After stirring the reaction mixture for 6.5 hr at 23° C., NaHCO$_3$ (aq) (5 mL) was added. The phases were separated and the aqueous phase was extracted with CH$_2$Cl$_2$ (3×5 mL). The combined organic phases were washed with brine (10 mL) and dried (MgSO$_4$). The filtrate was concentrated in vacuo and the residue was purified by column chromatography on silica gel eluting with hexanes/EtOAc to afford 546 mg of compound 3 (70% yield).

NMR Spectroscopy: $^1$H NMR (300 MHz, DMSO-d6, 23° C., δ): 8.10 (d, J=7.8 Hz, 1H), 7.82-7.65 (m, 2H), 7.60-7.35 (m, 5H), 4.60 (br s, 1H), 2.80-2.40 (m, 2H), 1.33 (s, 9H), 1.27 (br s, 1H). $^{19}$F NMR (282 MHz, DMSO-d6, 23° C., δ): −63.0 (br s, 3F), −116.0 (br s, 1F).

(S)-2-(1-amino-3,3,3-trifluoropropyl)-5-fluoro-3-phenylquinazolin-4(3H)-one (5)

Under ambient atmosphere, to (S)-tert-butyl (4,4,4-trifluoro-1-(2-fluoro-6-nitro-N-phenylbenzamido)-1-oxobutan-2-yl)carbamate (3) (546 mg, 1.09 mmol, 1.00 equiv) in AcOH (3.0 mL) at 23° C. was added Zn powder (428 mg, 6.54 mmol, 6.00 equiv). After stirring for 4 hr at 23° C., the reaction mixture was filtered and the filtrate was concentrated in vacuo to give crude compound 4.

Under nitrogen, to crude compound 4 obtained above in CH$_2$Cl$_2$ (3.0 mL) at 23° C. was added TFA (3.0 mL). After stirring for 20 min at 23° C., the reaction mixture was concentrated in vacuo. Aqueous K$_2$CO$_3$ solution (3.0 mL) was added to the residue and was extracted with CH$_2$Cl$_2$ (3×3.0 mL). The combined organic phases were washed with brine (3.0 mL) and dried (MgSO$_4$). The filtrate was concentrated in vacuo and the residue was purified by column chromatography on silica gel eluting with hexanes/EtOAc to afford 187 mg of compound 5 as a colorless solid (49% yield, 2 steps).

NMR Spectroscopy: $^1$H NMR (300 MHz, CDCl$_3$, 23° C., δ): 7.76-7.67 (m, 1H), 7.61-7.48 (m, 4H), 7.36-7.30 (m, 1H), 7.26-7.20 (m, 1H), 7.13 (t, J=8.4 Hz, 1H), 3.87 (t, J=6.3 Hz, 1H), 3.01-2.80 (m, 1H), 2.51-2.35 (m, 1H), 1.80 (br s, 2H). $^{19}$F NMR (282 MHz, CDCl$_3$, 23° C., δ): −63.8 (s, 3F), −109.7 (m, 1F).

(S)-2-(1-((9H-purin-6-yl)amino)-3,3,3-trifluoropropyl)-5-fluoro-3-phenylquinazolin-4(3H)-one (2A)

Under nitrogen, to (S)-2-(1-amino-3,3,3-trifluoropropyl)-5-fluoro-3-phenylquinazolin-4(3H)-one (5) (35 mg, 0.10 mmol, 1.0 equiv) in t-BuOH (0.5 mL) at 23° C. was added 6-bromo-9H-purine (6) (30 mg, 0.15 mmol, 1.5 equiv) and diisopropylethylamine (35 μL, 0.20 mmol, 2.0 equiv). After stirring for 3 days at 80° C. in a sealed tube, the reaction mixture was concentrated in vacuo and the residue was purified by preparative TLC eluting with CH$_2$Cl$_2$/MeOH to afford 10 mg of compound 2A as a colorless solid (21%).

NMR Spectroscopy: $^1$H NMR (300 MHz, CD$_3$OD, 23° C., δ): 8.10 (s, 2H), 7.82-7.78 (m, 1H), 7.62-7.20 (m, 7H), 5.62 (br s, 1H), 3.22-3.08 (m, 1H), 2.90-2.70 (m, 1H). $^{19}$F NMR (282 MHz, CD$_3$OD, 23° C., δ): −65.4 (s, 3F), −112.2 (m, 1F).

Example 1C

Synthesis of (S)-2-(1-((7H-pyrrolo[2,3-d]pyrimidin-4-yl)amino)-3,3,3-trifluoropropyl)-5-fluoro-3-phenylquinazolin-4(3H)-one (Compound 3A)

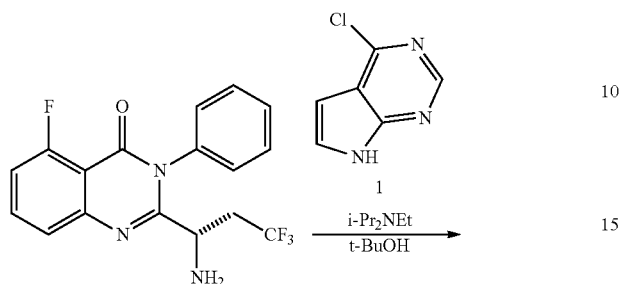

5 (from Example 1B)

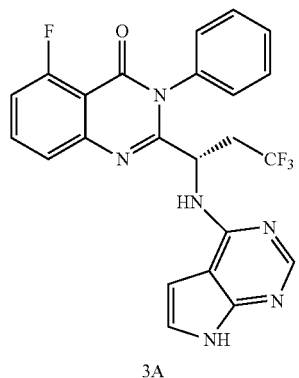

3A

Under nitrogen, to (S)-2-(1-amino-3,3,3-trifluoropropyl)-5-fluoro-3-phenylquinazolin-4(3H)-one (5 from Example 1B) (30 mg, 0.085 mmol, 1.0 equiv) in t-BuOH (0.5 mL) at 23° C. was added 4-chloro-7H-pyrrolo[2,3-d]pyrimidine (1) (20 mg, 0.13 mmol, 1.5 equiv and diisopropylethylamine (30 μL, 0.17 mmol, 2.0 equiv). After stirring for 24 hr at 140° C. in a sealed tube, the reaction mixture was concentrated in vacuo and the residue was purified by preparative TLC eluting with CH$_2$Cl$_2$/MeOH to afford 10 mg of compound 3A, as a colorless solid (19%).

NMR Spectroscopy: $^1$H NMR (400 MHz, CD$_3$OD, 23° C., δ): 7.87 (s, 1H), 7.78-7.69 (m, 1H), 7.52-7.47 (m, 2H), 7.38-7.26 (m, 3H), 7.18-7.09 (m, 2H), 6.99 (d, J=3.2 Hz, 1H), 6.48 (d, J=3.2 Hz, 1H), 5.52-5.46 (m, 1H), 3.16-3.03 (m, 1H), 2.83-2.65 (m, 1H). $^{19}$F NMR (375 MHz, CD$_3$OD, 23° C., δ): -65.3 (s, 3F), -112.3 (m, 1F).

Example 1D

Synthesis of (S)-2-(1-((3H-imidazo[4,5-b]pyridin-7-yl)amino)propyl)-5-fluoro-3-phenylquinazolin-4(3H)-one (Compound 4A)

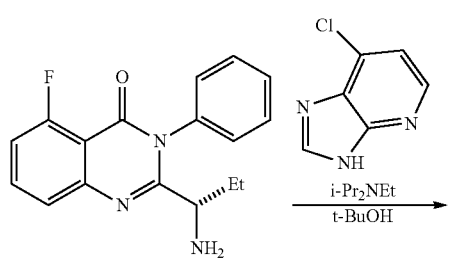

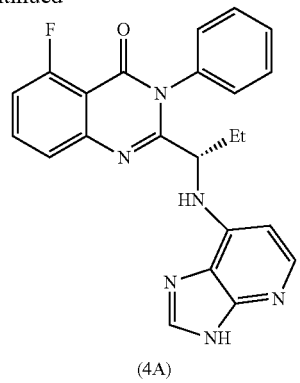

(4A)

Under nitrogen, to (S)-2-(1-aminopropyl)-5-fluoro-3-phenylquinazolin-4(3H)-one (27 mg, 0.091 mmol, 1.0 equiv) in t-BuOH (0.5 mL) at 23° C. is added 7-chloro-3H-imidazo[4,5-b]pyridine (21 mg, 0.14 mmol, 1.5 equiv) and diisopropylethylamine (63 μL, 0.36 mmol, 4.0 equiv). After stirring for 48 hr at 120° C. in a sealed tube, the reaction mixture is concentrated in vacuo and the residue is purified by preparative TLC eluting with CH$_2$Cl$_2$/MeOH to afford the title compound (Compound 4A).

Example 1E

Synthesis of (S)-2-(1-((1H-pyrrolo[2,3-b]pyridin-4-yl)amino)propyl)-5-fluoro-3-phenylquinazolin-4(3H)-one (Compound 5A)

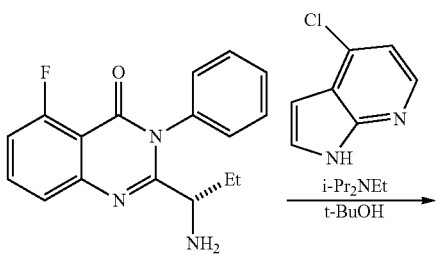

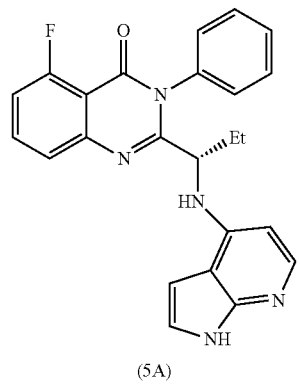

(5A)

Under nitrogen, to (S)-2-(1-aminopropyl)-5-fluoro-3-phenylquinazolin-4(3H)-one (27 mg, 0.091 mmol, 1.0 equiv) in t-BuOH (0.5 mL) at 23° C. is added 4-chloro-1H-pyrrolo[2,3-b]pyridine (21 mg, 0.14 mmol, 1.5 equiv) and diisopropylethylamine (63 μL, 0.36 mmol, 4.0 equiv). After stirring for 48 hr at 120° C. in a sealed tube, the reaction mixture is concentrated in vacuo and the residue is purified by preparative TLC eluting with CH$_2$Cl$_2$/MeOH to afford the title compound (Compound 5A).

Example 1F (S)-2-(1-((9H-purin-6-yl)amino)propyl)-5-fluoro-3-(3-(2,2,2-trifluoroethyl)phenyl)quinazolin-4(3H)-one (Compound 6A)

2-fluoro-6-nitro-N-(3-(2,2,2-trifluoroethyl)phenyl)benzamide

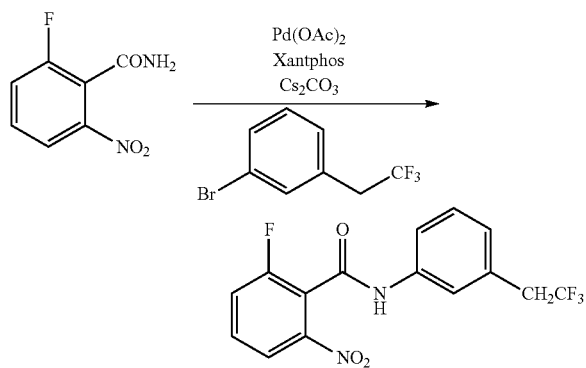

Under nitrogen, to 2-fluoro-6-nitrobenzamide (921 mg, 5.00 mmol, 1.00 equiv) in dioxane (5.0 mL) at 23° C. was added palladium acetate (225 mg, 1.00 mmol, 0.200 equiv), Xantphos (868 mg, 1.50 mmol, 0.300 equiv), cesium carbonate (2.28 g, 7.00 mmol, 1.40 equiv), and 1-bromo-3-(2,2,2-trifluoroethyl)benzene (1.31 g, 5.50 mmol, 1.10 equiv). After stirring for 16 hr at 100° C., the reaction mixture was concentrated in vacuo and the residue was purified by column chromatography eluting with EtOAc/hexanes to afford 860 mg of the title compound (50% yield).

NMR Spectroscopy: $^1$H NMR (400 MHz, CDCl$_3$, 23° C., δ): 8.00 (d, J=8.4 Hz, 1H), 7.69-7.55 (m, 3H), 7.50 (dd, J=8.8 Hz, 8.0 Hz, 1H), 7.42-7.36 (m, 1H), 7.15 (d, J=7.2 Hz, 1H), 3.39 (q, J=10.4 Hz, 2H). $^{19}$F NMR (375 MHz, CDCl$_3$, 23° C., δ): −65.7 (t, J=10.4 Hz, 3F), −111.9 (m, 1F).

(S)-2-(1-aminopropyl)-5-fluoro-3-(3-(2,2,2-trifluoroethyl)phenyl)quinazolin-4(3H)-one

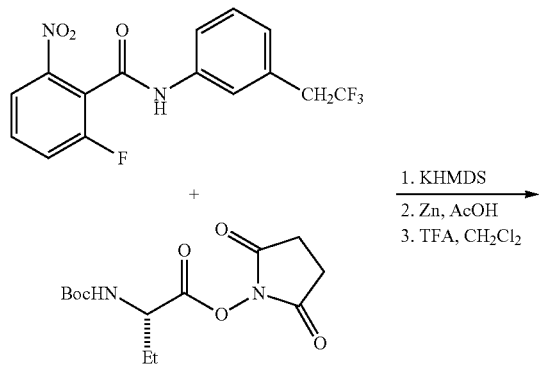

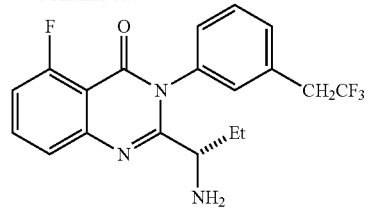

Under nitrogen, to 2-fluoro-6-nitro-N-(3-(2,2,2-trifluoroethyl)phenyl)benzamide (1.2 g, 3.51 mmol, 1.00 equiv) in THF (17.5 mL) at 0° C. was added KHMDS (1.0 M in THF, 3.51 mL, 3.5 mmol, 1.0 equiv). After stirring for 5 min at 0° C., (S)-2,5-dioxopyrrolidin-1-yl 2-((tert-butoxycarbonyl)amino)butanoate (1.05 g, 3.51 mmol, 1.00 equiv) was added to the reaction mixture. After stirring for 30 min at 0° C., water (20 mL) was added to the reaction mixture. The phases were separated and the aqueous phase was extracted with EtOAc (3×15 mL). The combined organic phases were washed with brine (30 mL) and dried (MgSO$_4$). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (17.5 mL) at 23° C. was added Zn powder (1.37 g, 20.9 mmol, 6.00 equiv). After stirring for 4 hr at 23° C., the reaction mixture was filtered and the filtrate was concentrated in vacuo to afford a crude quinazolinone, which was used in the next step without further purification.

Under nitrogen, to the crude material obtained above in CH$_2$Cl$_2$ (5.0 mL) at 23° C. was added TFA (5.0 mL). After stirring for 30 min at 23° C., the reaction mixture was concentrated in vacuo. Aqueous K$_2$CO$_3$ solution (5.0 mL) was added to the residue and was extracted with CH$_2$Cl$_2$ (3×5.0 mL). The combined organic phases were washed with brine (5.0 mL) and dried (MgSO$_4$). The filtrate was concentrated in vacuo and the residue was purified by column chromatography on silica gel eluting with hexanes/EtOAc to afford 320 mg of the title compound (24% yield over 3 steps).

NMR Spectroscopy: $^1$H NMR (300 MHz, CDCl$_3$, 23° C., δ): 7.77-7.63 (m, 1H), 7.60-7.42 (m, 3H), 7.31-7.20 (m, 2H), 7.12 (dd, J=9.0 Hz, 8.1 Hz, 1H), 3.42 (q, J=10.4 Hz, 2H) 3.42-3.35 (m, 1H), 1.98 (s br, 2H), 1.90-1.70 (m, 1H), 1.60-1.40 (m, 1H), 0.83-0.72 (m, 3H). $^{19}$F NMR (282 MHz, CDCl$_3$, 23° C., δ): −65.8 (m, 3F), −109.9 (m, 1F).

(S)-2-(1-((9H-purin-6-yl)amino)propyl)-5-fluoro-3-(3-(2,2,2-trifluoroethyl)phenyl)quinazolin-4(3H)-one

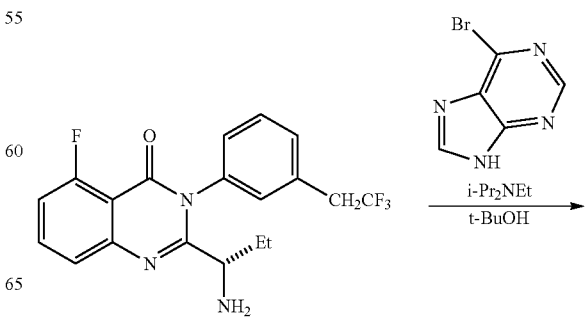

-continued

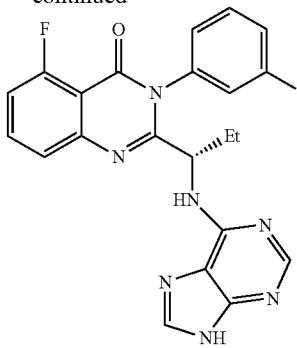

Under nitrogen, to (S)-2-(1-aminopropyl)-5-fluoro-3-(3-(2,2,2-trifluoroethyl)phenyl)quinazolin-4(3H)-one (38 mg, 0.10 mmol, 1.0 equiv) in t-BuOH (0.2 mL) at 23° C. was added 6-bromo-9H-purine (24 mg, 0.12 mmol, 1.2 equiv) and diisopropylethylamine (35 μL, 0.20 mmol, 2.0 equiv). After stirring for 24 hr at 120° C. in a sealed tube, the reaction mixture was concentrated in vacuo and the residue was purified by preparative TLC eluting with CH$_2$Cl$_2$/MeOH to afford 19 mg of the title compound (38% yield).

NMR Spectroscopy: $^1$H NMR (300 MHz, CDCl$_3$, 23° C., δ): 8.37-8.30 (m, 1H), 8.00 (s br, 1H), 7.70-7.43 (m, 4H), 7.40-7.30 (m, 1H), 7.12 (dd, J=9.0 Hz, 8.4 Hz, 1H), 6.74 (d, J=8.4 Hz, 1H), 5.30-5.00 (m, 1H), 3.52-3.35 (m, 2H), 1.99-1.70 (m, 2H), 0.89-0.79 (m, 3H). $^{19}$F NMR (282 MHz, CDCl$_3$, 23° C., δ): −65.7 (m, 3F), −109.9 (m, 1F).

Example 1G

Synthesis of (S)-2-(1-((7H-pyrrolo[2,3-d]pyrimidin-4-yl)amino)propyl)-5-fluoro-3-(3-(2,2,2-trifluoroethyl)phenyl)quinazolin-4(3H)-one (Compound 7A)

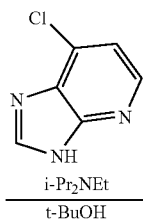

Under nitrogen, to (S)-2-(1-aminopropyl)-5-fluoro-3-(3-(2,2,2-trifluoroethyl)phenyl)quinazolin-4(3H)-one (38 mg, 0.10 mmol, 1.0 equiv) in t-BuOH (0.2 mL) at 23° C. was added 4-chloro-7H-pyrrolo[2,3-d]pyrimidine (18 mg, 0.12 mmol, 1.2 equiv) and diisopropylethylamine (35 μL, 0.20 mmol, 2.0 equiv). After stirring for 48 hr at 120° C. in a sealed tube, the reaction mixture was concentrated in vacuo and the residue was purified by preparative TLC eluting with CH$_2$Cl$_2$/MeOH to afford 19 mg of the title compound (38% yield).

NMR Spectroscopy: $^1$H NMR (300 MHz, CD$_3$OD, 23° C., δ): 8.02-7.95 (m, 1H), 7.80-7.66 (m, 1H), 7.62-7.39 (m, 5H), 7.22-7.02 (m, 2H), 6.61-6.58 (m, 1H), 3.63 (q, J=10.5 Hz, 2H), 3.10-2.90 (m, 1H), 2.19-1.81 (m, 2H), 0.97-0.82 (m, 3H). $^{19}$F NMR (282 MHz, CD$_3$OD, 23° C., δ): −67.3 (m, 3F), −112.5 (m, 1F).

Example 1H

Synthesis of (S)-2-(1-((3H-imidazo[4,5-b]pyridin-7-yl)amino)propyl)-5-fluoro-3-(3-(2,2,2-trifluoroethyl)phenyl)quinazolin-4(3H)-one (Compound 8A)

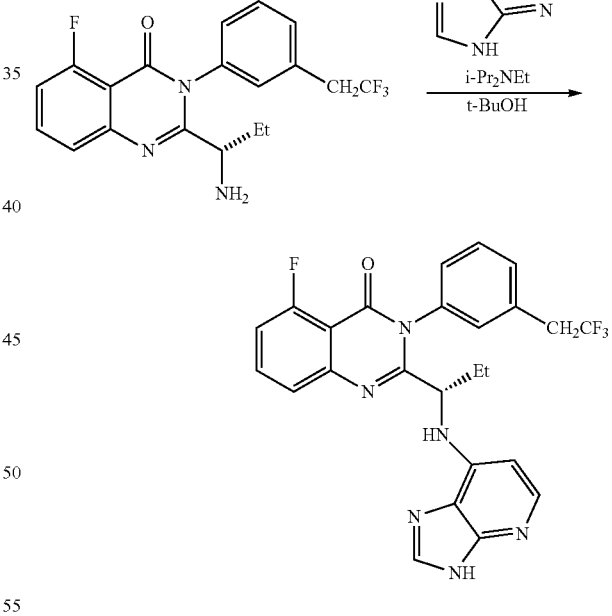

(8A)

Under nitrogen, to (S)-2-(1-aminopropyl)-5-fluoro-3-(3-(2,2,2-trifluoroethyl)phenyl)quinazolin-4(3H)-one (38 mg, 0.10 mmol, 1.0 equiv) in t-BuOH (0.5 mL) at 23° C. is added 7-chloro-3H-imidazo[4,5-b]pyridine (23 mg, 0.15 mmol, 1.5 equiv) and diisopropylethylamine (63 μL, 0.36 mmol, 4.0 equiv). After stirring for 48 hr at 120° C. in a sealed tube, the reaction mixture is concentrated in vacuo and the residue is purified by preparative TLC eluting with CH$_2$Cl$_2$/MeOH to afford the title compound.

Example 1I

Synthesis of (S)-2-(1-(((1H-pyrrolo[2,3-b]pyridin-4-yl)amino)propyl)-5-fluoro-3-(3-(2,2,2-trifluoroethyl)phenyl)quinazolin-4(3H)-one (Compound 9A)

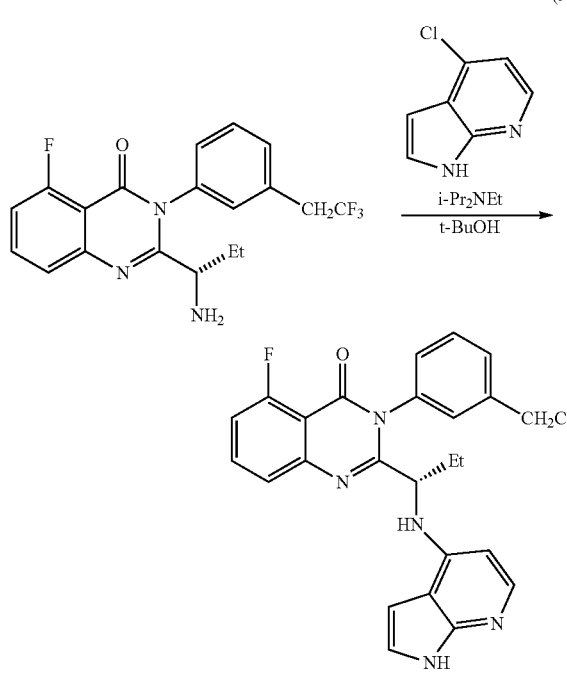

(9A)

Under nitrogen, to (S)-2-(1-aminopropyl)-5-fluoro-3-(3-(2,2,2-trifluoroethyl)phenyl)quinazolin-4(3H)-one (38 mg, 0.10 mmol, 1.0 equiv) in t-BuOH (0.5 mL) at 23° C. is added 4-chloro-1H-pyrrolo[2,3-b]pyridine (23 mg, 0.15 mmol, 1.5 equiv) and diisopropylethylamine (63 μL, 0.36 mmol, 4.0 equiv). After stirring for 48 hr at 120° C. in a sealed tube, the reaction mixture is concentrated in vacuo and the residue is purified by preparative TLC eluting with CH$_2$Cl$_2$/MeOH to afford the title compound (Compound 9A).

Example 1J (S)-2-(1-((9H-purin-6-yl)amino)propyl)-5-fluoro-3-(3-(2,2,2-trifluoroethoxy)phenyl)quinazolin-4(3H)-one (Compound 10A)

2-fluoro-6-nitro-N-(3-(2,2,2-trifluoroethoxy)phenyl)benzamide

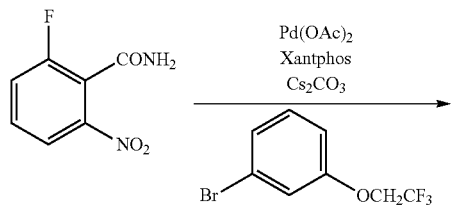

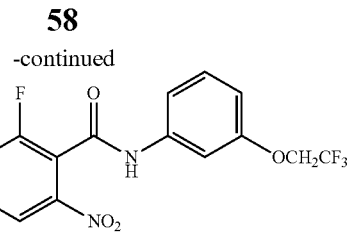

Under nitrogen, to 2-fluoro-6-nitrobenzamide (710 mg, 3.86 mmol, 1.00 equiv) in dioxane (3.9 mL) at 23° C. was added palladium acetate (173 mg, 0.772 mmol, 0.200 equiv), Xantphos (670 mg, 1.16 mmol, 0.300 equiv), cesium carbonate (1.76 g, 5.4 mmol, 1.40 equiv), and 1-bromo-3-(2,2,2-trifluoroethoxy)benzene (1.08 g, 4.25 mmol, 1.10 equiv). After stirring for 8 hr at 100° C., the reaction mixture was concentrated in vacuo and the residue was purified by column chromatography eluting with EtOAc/hexanes to afford 810 mg of the title compound (59% yield).

NMR Spectroscopy: $^1$H NMR (300 MHz, CDCl$_3$, 23° C., δ): 7.95 (d, J=8.4 Hz, 1H), 7.91 (s br, 1H), 7.62-7.25 (m, 4H), 7.06 (d, J=8.1 Hz, 1H), 6.77 (dd, J=8.4 Hz, 2.4 Hz, 1H), 4.36 (q, J=8.1 Hz, 2H). $^{19}$F NMR (282 MHz, CDCl$_3$, 23° C., δ): −73.9 (t, J=8.1 Hz, 3F), −112.0 (m, 1F).

(S)-2-(1-aminopropyl)-5-fluoro-3-(3-(2,2,2-trifluoroethoxy)phenyl)quinazolin-4(3H)-one

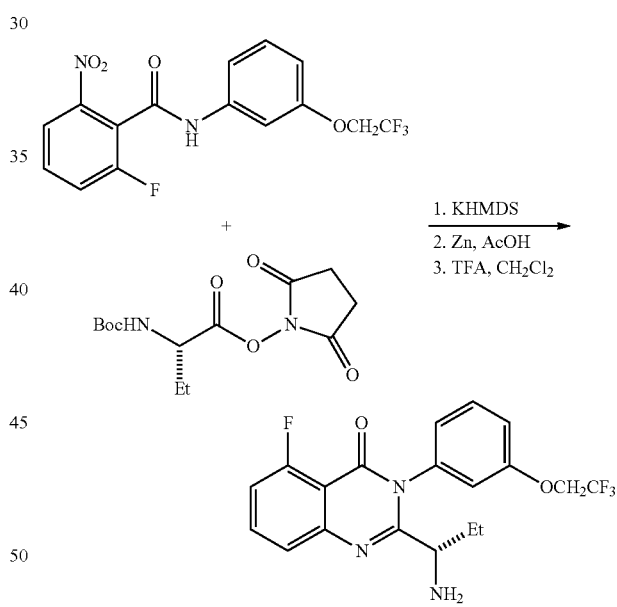

Under nitrogen, to 2-fluoro-6-nitro-N-(3-(2,2,2-trifluoroethoxy)phenyl)benzamide (810 mg, 2.26 mmol, 1.00 equiv) in THF (11 mL) at 0° C. was added KHMDS (1.0 M in THF, 2.26 mL, 2.3 mmol, 1.0 equiv). After stirring for 5 min at 0° C., (S)-2,5-dioxopyrrolidin-1-yl 2-((tert-butoxycarbonyl)amino)butanoate (679 mg, 2.26 mmol, 1.00 equiv) was added to the reaction mixture. After stirring for 30 min at 0° C., water (10 mL) was added to the reaction mixture. The phases were separated and the aqueous phase was extracted with EtOAc (3×10 mL). The combined organic phases were washed with brine (20 mL) and dried (MgSO$_4$). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (11 mL) at 23° C. was added Zn powder (1.48 g, 22.6 mmol, 10.0 equiv). After stirring for 1 hr at 23° C., the reaction mixture was filtered and the filtrate was concentrated in vacuo to afford a crude quinazolinone, which was used in the next step without further purification.

Under nitrogen, to the crude material obtained above in CH$_2$Cl$_2$ (5.0 mL) at 23° C. was added TFA (5.0 mL). After stirring for 30 min at 23° C., the reaction mixture was concentrated in vacuo. Aqueous K$_2$CO$_3$ solution (5.0 mL) was added to the residue and was extracted with CH$_2$Cl$_2$ (3×5.0 mL). The combined organic phases were washed with brine (5.0 mL) and dried (MgSO$_4$). The filtrate was concentrated in vacuo and the residue was purified by column chromatography on silica gel eluting with hexanes/EtOAc to afford 300 mg of the title compound (34% yield over 3 steps).

NMR Spectroscopy: $^1$H NMR (300 MHz, CDCl$_3$, 23° C., δ): 7.74-7.61 (m, 1H), 7.57-7.43 (m, 2H), 7.13-7.02 (m, 2H), 6.99-6.87 (m, 2H), 4.36 (q, J=8.4 Hz, 2H) 3.48-3.39 (m, 1H), 1.93 (s br, 2H), 1.90-1.72 (m, 1H), 1.60-1.45 (m, 1H), 0.86-0.75 (m, 3H). $^{19}$F NMR (282 MHz, CDCl$_3$, 23° C., δ): −73.9 (m, 3F), −109.9 (m, 1F).

(S)-2-(1-((9H-purin-6-yl)amino)propyl)-5-fluoro-3-(3-(2,2,2-trifluoroethoxy)phenyl)quinazolin-4(3H)-one

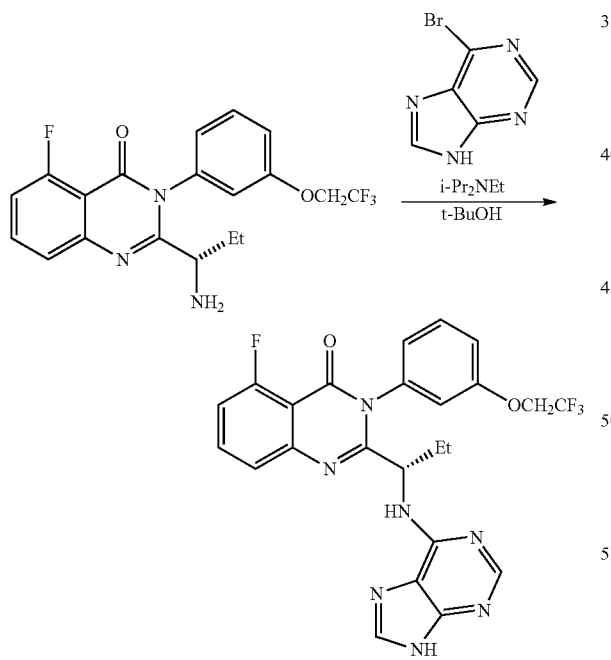

Under nitrogen, to (S)-2-(1-aminopropyl)-5-fluoro-3-(3-(2,2,2-trifluoroethoxy)phenyl)quinazolin-4(3H)-one (22 mg, 0.056 mmol, 1.0 equiv) in t-BuOH (0.11 mL) at 23° C. was added 6-bromo-9H-purine (13 mg, 0.067 mmol, 1.2 equiv) and diisopropylethylamine (19 μL, 0.11 mmol, 2.0 equiv). After stirring for 4.5 hr at 120° C. in a sealed tube, the reaction mixture was concentrated in vacuo and the residue was purified by preparative TLC eluting with CH$_2$Cl$_2$/MeOH to afford 4.1 mg of the title compound (14% yield).

NMR Spectroscopy: $^1$H NMR (300 MHz, CDCl$_3$, 23° C., δ): 8.79 (s, 1H), 8.39-8.28 (m, 2H), 8.02 (s br, 1H), 7.75-7.43 (m, 3H), 7.20-7.00 (m, 3H), 5.30-5.20 (m, 1H), 4.50-4.22 (m, 2H), 2.07-1.78 (m, 2H), 0.96-0.79 (m, 3H). $^{19}$F NMR (282 MHz, CDCl$_3$, 23° C., δ): −73.8 (m, 3F), −109.8 (m, 1F).

Example 1K

Synthesis of (S)-2-(1-((7H-pyrrolo[2,3-d]pyrimidin-4-yl)amino)propyl)-5-fluoro-3-(3-(2,2,2-trifluoroethoxy)phenyl)quinazolin-4(3H)-one (Compound 11A)

(S)-2-(1-((7H-pyrrolo[2,3-d]pyrimidin-4-yl)amino)propyl)-5-fluoro-3-(3-(2,2,2-trifluoroethoxy)phenyl)quinazolin-4(3H)-one

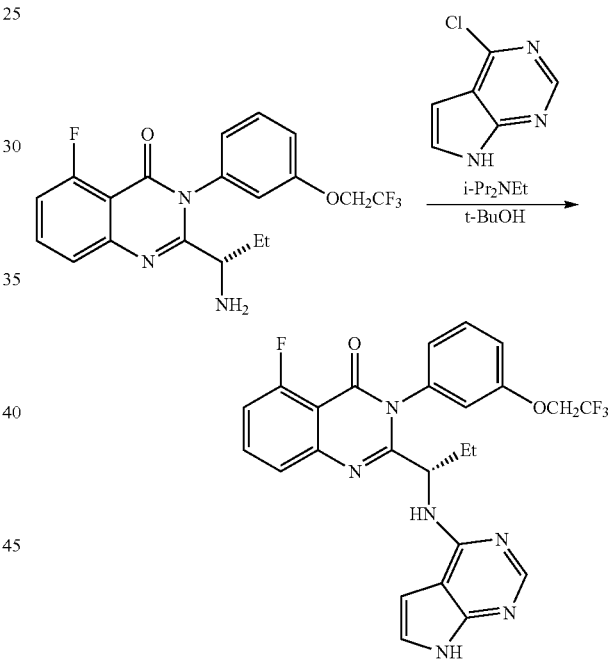

Under nitrogen, to (S)-2-(1-aminopropyl)-5-fluoro-3-(3-(2,2,2-trifluoroethoxy)phenyl)quinazolin-4(3H)-one (22 mg, 0.056 mmol, 1.0 equiv) in t-BuOH (0.11 mL) at 23° C. was added 4-chloro-7H-pyrrolo[2,3-d]pyrimidine (10 mg, 0.067 mmol, 1.2 equiv) and diisopropylethylamine (19 μL, 0.11 mmol, 2.0 equiv). After stirring for 14 hr at 120° C. in a sealed tube, the reaction mixture was concentrated in vacuo and the residue was purified by preparative TLC eluting with CH$_2$Cl$_2$/MeOH to afford 5.0 mg of the title compound.

NMR Spectroscopy: $^1$H NMR (300 MHz, CDCl$_3$, 23° C., δ): 8.23-8.20 (m, 1H), 7.70-7.43 (m, 3H), 7.22-7.00 (m, 5H), 6.42 (s br, 1H), 6.00-5.84 (m, 1H), 5.25-5.15 (m, 1H), 4.44-4.20 (m, 2H), 2.01-1.75 (m, 2H), 0.99-0.84 (m, 3H). $^{19}$F NMR (282 MHz, CDCl$_3$, 23° C., δ): −73.8 (m, 3F), −109.7 (m, 1F).

Example 1L

Synthesis of (S)-2-(1-((3H-imidazo[4,5-b]pyridin-7-yl)amino)propyl)-5-fluoro-3-(3-(2,2,2-trifluoroethoxy)phenyl)quinazolin-4(3H)-one (Compound 12A)

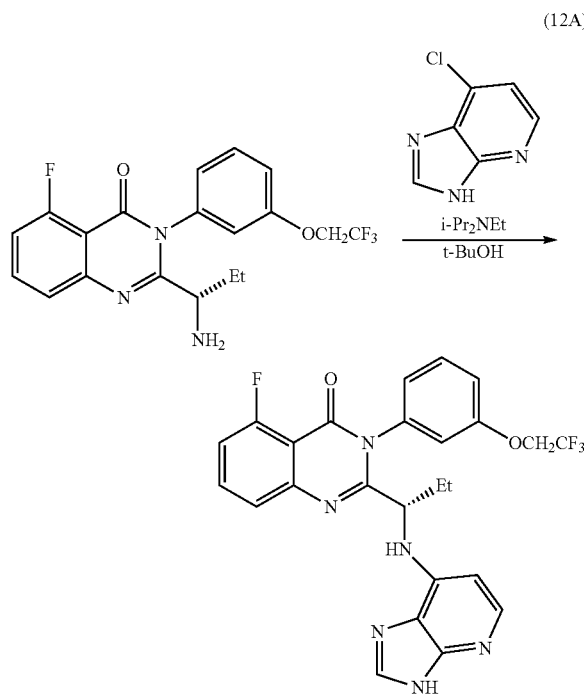

Under nitrogen, to (S)-2-(1-aminopropyl)-5-fluoro-3-(3-(2,2,2-trifluoroethoxy)phenyl)quinazolin-4(3H)-one (40 mg, 0.10 mmol, 1.0 equiv) in t-BuOH (0.5 mL) at 23° C. is added 7-chloro-3H-imidazo[4,5-b]pyridine (23 mg, 0.15 mmol, 1.5 equiv) and diisopropylethylamine (63 µL, 0.36 mmol, 4.0 equiv). After stirring for 48 hr at 120° C. in a sealed tube, the reaction mixture is concentrated in vacuo and the residue is purified by preparative TLC eluting with CH₂Cl₂/MeOH to afford the title compound (Compound 12A).

Example 1M

Synthesis of (S)-2-(1-((1H-pyrrolo[2,3-b]pyridin-4-yl)amino)propyl)-5-fluoro-3-(3-(2,2,2-trifluoroethoxy)phenyl)quinazolin-4(3H)-one (Compound 13A)

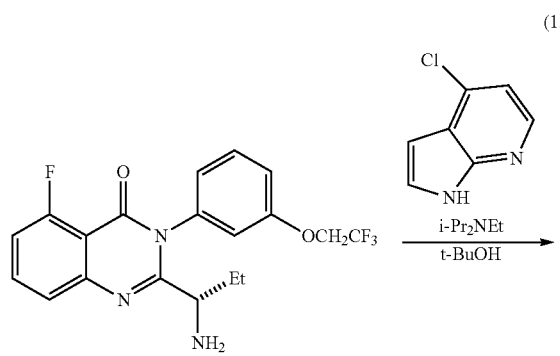

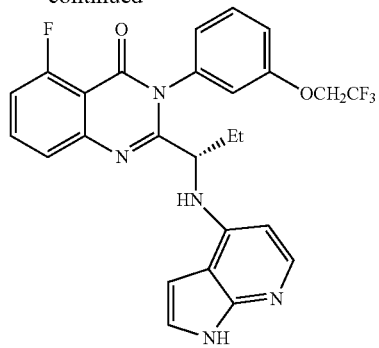

Under nitrogen, to (S)-2-(1-aminopropyl)-5-fluoro-3-(3-(2,2,2-trifluoroethoxy)phenyl)quinazolin-4(3H)-one (40 mg, 0.10 mmol, 1.0 equiv) in t-BuOH (0.5 mL) at 23° C. is added 4-chloro-1H-pyrrolo[2,3-b]pyridine (23 mg, 0.15 mmol, 1.5 equiv) and diisopropylethylamine (63 µL, 0.36 mmol, 4.0 equiv). After stirring for 48 hr at 120° C. in a sealed tube, the reaction mixture is concentrated in vacuo and the residue is purified by preparative TLC eluting with CH₂Cl₂/MeOH to afford the title compound (Compound 13A).

Example 1N

Synthesis of (S)-2-(1-((7H-pyrrolo[2,3-d]pyrimidin-4-yl)amino)ethyl)-5-fluoro-3-(3-(2,2,2-trifluoroethoxy)phenyl)quinazolin-4(3H)-one (Compound 14A)

(S)-2-(1-aminoethyl)-5-fluoro-3-(3-(2,2,2-trifluoroethoxy)phenyl)quinazolin-4(3H)-one

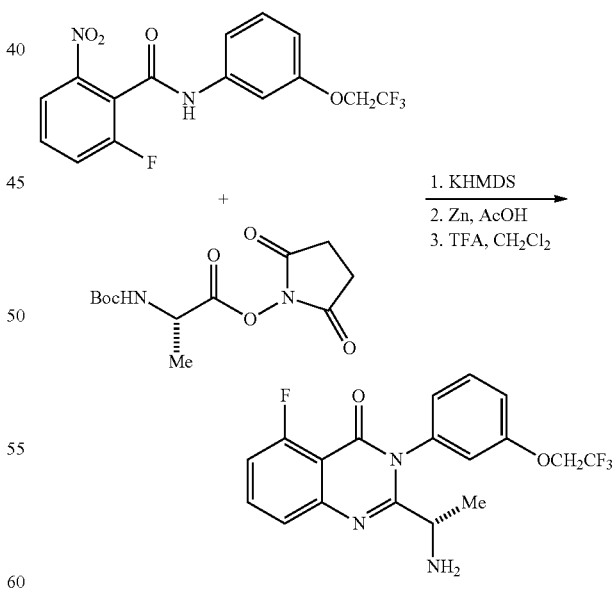

Under nitrogen, to 2-fluoro-6-nitro-N-(3-(2,2,2-trifluoroethoxy)phenyl)benzamide (400 mg, 1.12 mmol, 1.00 equiv) in THF (5.6 mL) at 0° C. was added KHMDS (1.0 M in THF, 1.12 mL, 1.1 mmol, 1.0 equiv). After stirring for 10 min at 0° C., (S)-2,5-dioxopyrrolidin-1-yl 2-((tert-butoxycarbonyl)amino)propanoate (321 mg, 1.12 mmol, 1.00 equiv) was added to the reaction mixture. After stirring for 30 min at 0° C., water (10 mL) was added to the reaction mixture. The phases were separated and the aqueous phase was extracted with EtOAc (3×10 mL). The combined organic phases were washed with brine (20 mL) and dried (MgSO₄). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (3.2 mL) at 23° C. was added Zn powder (208 mg, 3.17 mmol, 2.83 equiv). After stirring for 1 hr at 23° C., the reaction mixture was filtered and the filtrate was concentrated in vacuo to afford a crude quinazolinone, which was used in the next step without further purification.

Under nitrogen, to the crude material obtained above in CH₂Cl₂ (1.0 mL) at 23° C. was added TFA (1.0 mL). After stirring for 30 min at 23° C., the reaction mixture was concentrated in vacuo. Aqueous K₂CO₃ solution (3.0 mL) was added to the residue and was extracted with CH₂Cl₂ (3×3.0 mL). The combined organic phases were washed with brine (3.0 mL) and dried (MgSO₄). The filtrate was concentrated in vacuo and the residue was purified by column chromatography on silica gel eluting with hexanes/EtOAc to afford 50 mg of the title compound (12% yield over 3 steps).

NMR Spectroscopy: $^1$H NMR (300 MHz, CDCl₃, 23° C., δ): 7.76-7.69 (m, 1H), 7.57-7.49 (m, 2H), 7.18-7.08 (m, 2H), 7.01-6.88 (m, 2H), 4.39 (q, J=8.1 Hz, 2H) 3.78-3.69 (m, 1H), 2.11 (s br, 2H), 1.32-1.21 (m, 3H). $^{19}$F NMR (282 MHz, CDCl₃, 23° C., δ): −75.7 (m, 3F), −109.9 (m, 1F).

(S)-2-(1-((7H-pyrrolo[2,3-d]pyrimidin-4-yl)amino)ethyl)-5-fluoro-3-(3-(2,2,2-trifluoroethoxy)phenyl)quinazolin-4(3H)-one Under nitrogen, to (S)-2-(1-aminoethyl)-5-fluoro-3-(3-(2,2,2-trifluoroethoxy)phenyl)quinazolin-4(3H)-one (50 mg, 0.13 mmol, 1.0 equiv) in t-BuOH (0.13 mL) at 23° C. was added 4-chloro-7H-pyrrolo[2,3-d]pyrimidine (24 mg, 0.16 mmol, 1.2 equiv) and diisopropylethylamine (46 µL, 0.26 mmol, 2.0 equiv). After stirring for 16 hr at 120° C. in a sealed tube, the reaction mixture was concentrated in vacuo and the residue was purified by preparative TLC eluting with CH₂Cl₂/MeOH to afford 18 mg of the title compound (28% yield).

NMR Spectroscopy: $^1$H NMR (300 MHz, CD₃OD, 23° C., δ): 8.03-7.91 (m, 1H), 7.80-7.68 (m, 1H), 7.58-7.40 (m, 2H), 7.27-7.00 (m, 5H), 6.58 (s br, 1H), 5.21-5.05 (m, 1H), 4.62-4.50 (m, 1H), 4.30-3.80 (m, 1H), 1.56 (d, J=6.6 Hz, 3H). $^{19}$F NMR (282 MHz, CD₃OD, 23° C., δ): −75.8 (m, 3F), −112.3 (m, 1F).

Example 1O

Synthesis of (S)-2-(1-((7H-pyrrolo[2,3-d]pyrimidin-4-yl)amino)ethyl)-5-fluoro-3-(4-(2,2,2-trifluoroethoxy)phenyl)quinazolin-4(3H)-one (Compound 15A)

(S)-2-(1-aminoethyl)-5-fluoro-3-(4-(2,2,2-trifluoroethoxy)phenyl)quinazolin-4(3H)-one

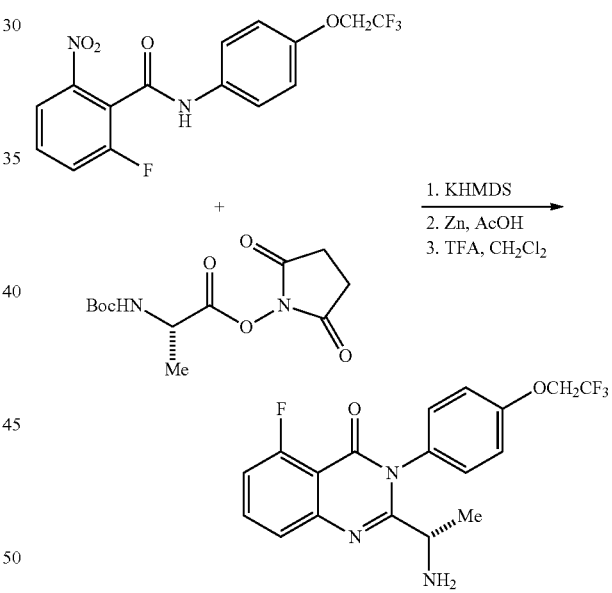

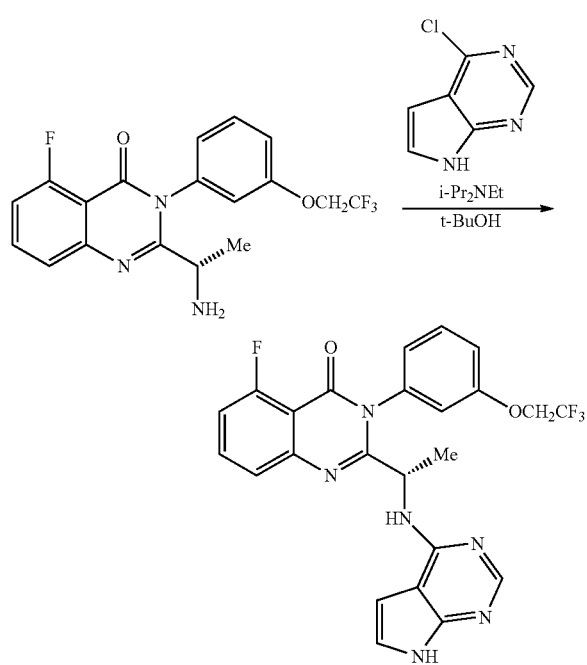

Under nitrogen, to 2-fluoro-6-nitro-N-(4-(2,2,2-trifluoroethoxy)phenyl)benzamide (150 mg, 0.419 mmol, 1.00 equiv) in THF (4.2 mL) at 0° C. was added KHMDS (1.0 M in THF, 0.42 mL, 0.42 mmol, 1.0 equiv). After stirring for 10 min at 0° C., (S)-2,5-dioxopyrrolidin-1-yl 2-((tert-butoxycarbonyl)amino)propanoate (132 mg, 0.461 mmol, 1.10 equiv) was added to the reaction mixture. After stirring for 30 min at 0° C., water (10 mL) was added to the reaction mixture. The phases were separated and the aqueous phase was extracted with EtOAc (3×10 mL). The combined organic phases were washed with brine (20 mL) and dried (MgSO₄). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (2.3 mL) at 23° C. was added Zn powder (224 mg, 3.43 mmol, 8.19 equiv). After stirring for 1 hr at 23° C., the reaction mixture was filtered and the filtrate was concentrated in vacuo to afford a crude quinazolinone, which was used in the next step without further purification.

Under nitrogen, to the crude material obtained above in CH$_2$Cl$_2$ (1.0 mL) at 23° C. was added TFA (1.0 mL). After stirring for 30 min at 23° C., the reaction mixture was concentrated in vacuo. Aqueous K$_2$CO$_3$ solution (3.0 mL) was added to the residue and was extracted with CH$_2$Cl$_2$ (3×3.0 mL). The combined organic phases were washed with brine (3.0 mL) and dried (MgSO$_4$). The filtrate was concentrated in vacuo and the residue was purified by column chromatography on silica gel eluting with hexanes/EtOAc to afford 25 mg of the title compound (16% yield over 3 steps).

NMR Spectroscopy: $^1$H NMR (300 MHz, CDCl$_3$, 23° C., δ): 7.76-7.63 (m, 1H), 7.61-7.48 (m, 2H), 7.30-7.20 (m, 2H), 7.18-7.04 (m, 2H), 4.41 (q, J=8.1 Hz, 2H) 3.79-3.68 (m, 1H), 3.11 (s br, 2H), 1.32-1.21 (m, 3H). $^{19}$F NMR (282 MHz, CDCl$_3$, 23° C., δ): −73.8 (m, 3F), −109.9 (m, 1F).

(S)-2-(1-((7H-pyrrolo[2,3-d]pyrimidin-4-yl)amino)ethyl)-5-fluoro-3-(4-(2,2,2-trifluoroethoxy)phenyl)quinazolin-4(3H)-one

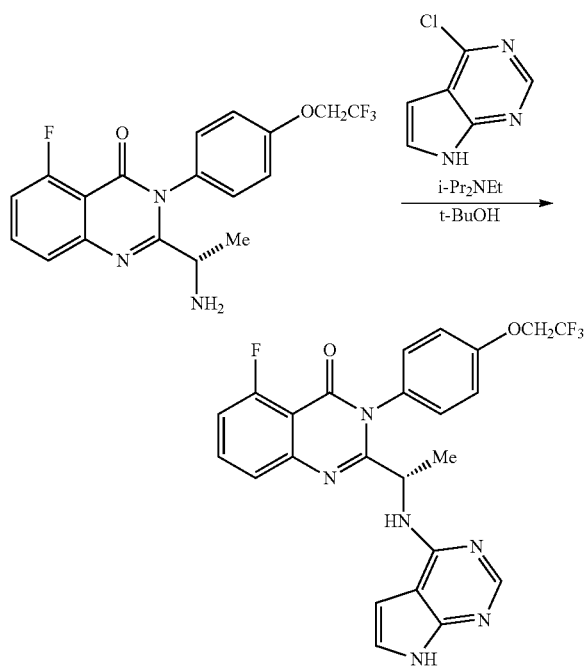

Under nitrogen, to (S)-2-(1-amino ethyl)-5-fluoro-3-(3-(2,2,2-trifluoroethoxy)phenyl)quinazolin-4(3H)-one (25 mg, 0.066 mmol, 1.0 equiv) in t-BuOH (0.07 mL) at 23° C. was added 4-chloro-7H-pyrrolo[2,3-d]pyrimidine (12 mg, 0.079 mmol, 1.2 equiv) and diisopropylethylamine (23 μL, 0.13 mmol, 2.0 equiv). After stirring for 16 hr at 120° C. in a sealed tube, the reaction mixture was concentrated in vacuo and the residue was purified by preparative TLC eluting with CH$_2$Cl$_2$/MeOH to afford 5.0 mg of the title compound (15% yield).

NMR Spectroscopy: $^1$H NMR (300 MHz, CD$_3$OD, 23° C., δ): 8.00 (s, 1H), 7.80-7.71 (m, 1H), 7.58-7.35 (m, 5H), 7.22-7.00 (m, 2H), 6.60 (s br, 1H), 5.02-4.92 (m, 2H), 4.62-4.50 (m, 1H), 1.56 (d, J=6.6 Hz, 3H). $^{19}$F NMR (282 MHz, CD$_3$OD, 23° C., δ): −75.7 (m, 3F), −112.5 (m, 1F).

Example 1P

Synthesis of (S)-2-(1-((7H-pyrrolo[2,3-d]pyrimidin-4-yl)amino)propyl)-5-fluoro-3-(4-(2,2,2-trifluoroethoxy)phenyl)quinazolin-4(3H)-one (Compound 16A)

(S)-2-(1-aminopropyl)-5-fluoro-3-(4-(2,2,2-trifluoroethoxy)phenyl)quinazolin-4(3H)-one

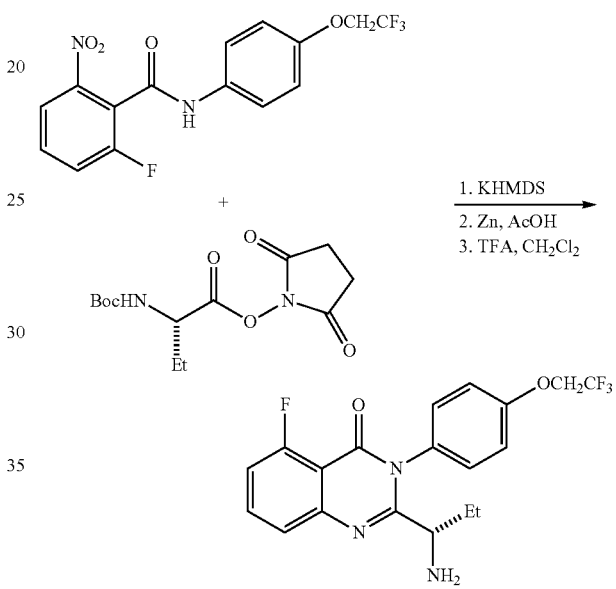

Under nitrogen, to 2-fluoro-6-nitro-N-(4-(2,2,2-trifluoroethoxy)phenyl)benzamide (150 mg, 0.419 mmol, 1.00 equiv) in THF (4.2 mL) at 0° C. was added KHMDS (1.0 M in THF, 0.42 mL, 0.42 mmol, 1.0 equiv). After stirring for 10 min at 0° C., (S)-2,5-dioxopyrrolidin-1-yl 2-((tert-butoxycarbonyl)amino)butanoate (138 mg, 0.461 mmol, 1.10 equiv) was added to the reaction mixture. After stirring for 30 min at 0° C., water (10 mL) was added to the reaction mixture. The phases were separated and the aqueous phase was extracted with EtOAc (3×10 mL). The combined organic phases were washed with brine (20 mL) and dried (MgSO$_4$). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (2.3 mL) at 23° C. was added Zn powder (224 mg, 3.43 mmol, 8.19 equiv). After stirring for 1 hr at 23° C., the reaction mixture was filtered and the filtrate was concentrated in vacuo to afford a crude quinazolinone, which was used in the next step without further purification.

Under nitrogen, to the crude material obtained above in CH$_2$Cl$_2$ (1.0 mL) at 23° C. was added TFA (1.0 mL). After stirring for 30 min at 23° C., the reaction mixture was concentrated in vacuo. Aqueous K₂CO₃ solution (3.0 mL) was added to the residue and was extracted with CH₂Cl₂ (3×3.0 mL). The combined organic phases were washed with brine (3.0 mL) and dried (MgSO₄). The filtrate was concentrated in vacuo and the residue was purified by column chromatography on silica gel eluting with hexanes/ EtOAc to afford 35 mg of the title compound (22% yield over 3 steps).

NMR Spectroscopy: ¹H NMR (300 MHz, CDCl₃, 23° C., δ): 7.76-7.61 (m, 1H), 7.60-7.48 (m, 2H), 7.35-7.18 (m, 2H), 7.17-7.04 (m, 2H), 4.41 (q, J=8.1 Hz, 2H), 3.43-3.39 (m, 1H), 1.84 (s br, 2H), 1.82-1.41 (m, 2H), 0.84-0.78 (m, 3H). ¹⁹F NMR (282 MHz, CDCl₃, 23° C., δ): −73.9 (m, 3F), −110.0 (m, 1F).

(S)-2-(1-((7H-pyrrolo[2,3-d]pyrimidin-4-yl)amino) propyl)-5-fluoro-3-(4-(2,2,2-trifluoroethoxy)phenyl) quinazolin-4(3H)-one

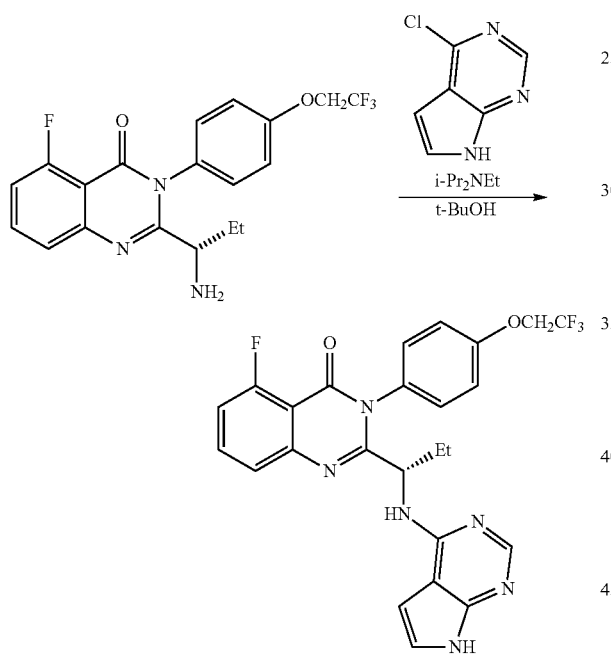

Under nitrogen, to (S)-2-(1-aminopropyl)-5-fluoro-3-(4- (2,2,2-trifluoroethoxy)phenyl)quinazolin-4(3H)-one (35 mg, 0.089 mmol, 1.0 equiv) in t-BuOH (0.09 mL) at 23° C. was added 4-chloro-7H-pyrrolo[2,3-d]pyrimidine (16 mg, 0.11 mmol, 1.2 equiv) and diisopropylethylamine (31 µL, 0.18 mmol, 2.0 equiv). After stirring for 16 hr at 120° C. in a sealed tube, the reaction mixture was concentrated in vacuo and the residue was purified by preparative TLC eluting with CH₂Cl₂/MeOH to afford 6.1 mg of the title compound (13% yield).

NMR Spectroscopy: ¹H NMR (300 MHz, CD₃OD, 23° C., δ): 8.00-7.91 (m, 1H), 7.80-7.71 (m, 1H), 7.58-7.42 (m, 2H), 7.22-7.00 (m, 5H), 6.60 (s br, 1H), 5.20-4.99 (m, 1H), 4.61-4.50 (m, 2H), 4.28-3.80 (m, 2H), 1.57 (d, J=6.6 Hz, 3H). ¹⁹F NMR (282 MHz, CD₃OD, 23° C., δ): −75.7 (m, 3F), −112.3 (m, 1F).

Example 1Q

Synthesis of (S)-5-fluoro-2-(1-((5-fluoro-7H-pyrrolo [2,3-d]pyrimidin-4-yl)amino)ethyl)-3-(3-(2,2,2-trifluoroethoxy)phenyl)quinazolin-4(3H)-one (Compound 17A)

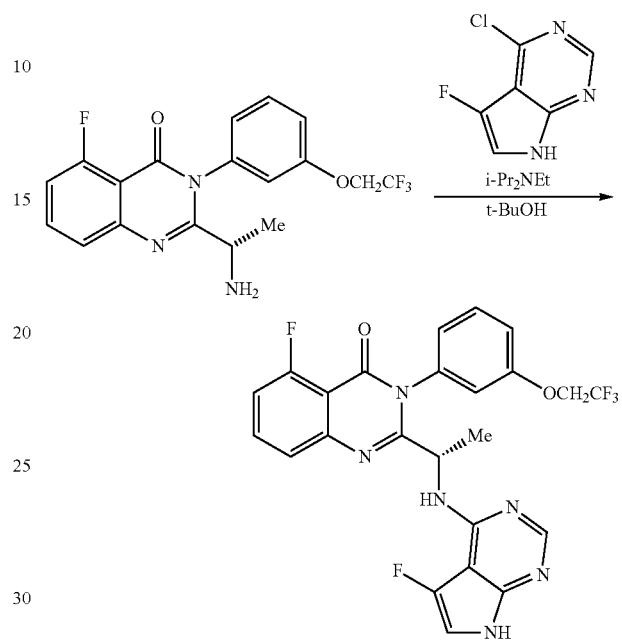

Under nitrogen, to (S)-2-(1-aminoethyl)-5-fluoro-3-(3-(2, 2,2-trifluoroethoxy)phenyl)quinazolin-4(3H)-one (76 mg, 0.20 mmol, 1.0 equiv) in t-BuOH (0.4 mL) at 23° C. was added 4-chloro-5-fluoro-7H-pyrrolo[2,3-d]pyrimidine (38 mg, 0.22 mmol, 1.1 equiv) and diisopropylethylamine (70 µL, 0.40 mmol, 2.0 equiv). After stirring for 16 hr at 120° C. in a sealed tube, the reaction mixture was concentrated in vacuo and the residue was purified by preparative TLC eluting with CH₂Cl₂/MeOH to afford 43 mg of the title compound (42% yield).

NMR Spectroscopy: ¹H NMR (300 MHz, CD₃OD, 23° C., δ): 7.94-7.88 (m, 1H), 7.77-7.62 (m, 1H), 7.58-7.28 (m, 2H), 7.20-7.00 (m, 4H), 6.80 (s br, 1H), 5.18-5.02 (m, 1H), 4.60-4.15 (m, 2H), 1.55-1.40 (m, 3H). ¹⁹F NMR (282 MHz, CD₃OD, 23° C., δ): −75.7 (m, 3F), −112.3 (m, 1F), −171.4 (s br, 1F).

Example 1R

Synthesis of (S)-5-fluoro-3-(3-(2,2,2-trifluoroethoxy)phenyl)-2-(1-((5-(trifluoromethyl)-7H-pyrrolo [2,3-d]pyrimidin-4-yl)amino)ethyl)quinazolin-4 (3H)-one (Compound 18A)

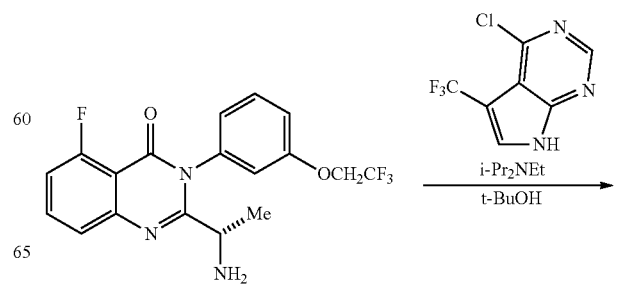

-continued

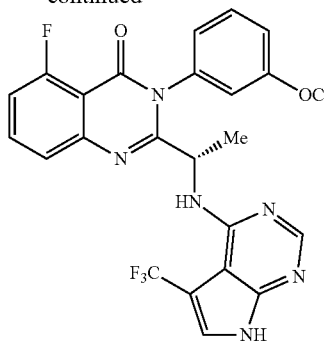

Under nitrogen, to (S)-2-(1-aminoethyl)-5-fluoro-3-(3-(2,2,2-trifluoroethoxy)phenyl)quinazolin-4(3H)-one (76 mg, 0.20 mmol, 1.0 equiv) in t-BuOH (0.4 mL) at 23° C. was added 4-chloro-5-(trifluoromethyl)-7H-pyrrolo[2,3-d]pyrimidine (49 mg, 0.22 mmol, 1.1 equiv) and diisopropylethylamine (70 µL, 0.40 mmol, 2.0 equiv). After stirring for 16 hr at 120° C. in a sealed tube, the reaction mixture was concentrated in vacuo and the residue was purified by preparative TLC eluting with $CH_2Cl_2$/MeOH to afford 50 mg of the title compound (44% yield).

NMR Spectroscopy: $^1$H NMR (300 MHz, $CD_3OD$, 23° C., δ): 8.10-8.01 (m, 1H), 7.81-7.72 (m, 1H), 7.59-7.43 (m, 2H), 7.30-7.00 (m, 5H), 5.20-5.06 (m, 1H), 4.63-4.00 (m, 2H), 1.60-1.53 (m, 3H). $^{19}$F NMR (282 MHz, $CD_3OD$, 23° C., δ): −62.5 (m, 3F), −75.7 (m, 3F), −112.4 (m, 1F).

Example 1S

Synthesis of (S)-2-(1-((7H-pyrrolo[2,3-d]pyrimidin-4-yl)amino)ethyl)-5-fluoro-3-(3-(2,2,3,3,3-pentafluoropropoxy)phenyl)quinazolin-4(3H)-one (Compound 19A)

2-fluoro-6-nitro-N-(3-(2,2,3,3,3-pentafluoropropoxy)phenyl)benzamide

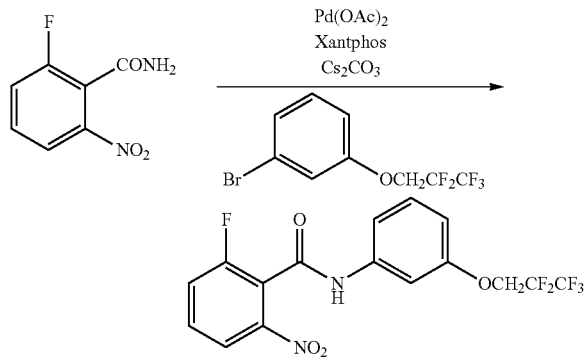

Under nitrogen, to 2-fluoro-6-nitrobenzamide (1.15 g, 6.23 mmol, 1.00 equiv) in dioxane (6.2 mL) at 23° C. was added palladium acetate (140 mg, 0.623 mmol, 0.100 equiv), Xantphos (541 mg, 0.935 mmol, 0.150 equiv), cesium carbonate (1.21 g, 8.72 mmol, 1.40 equiv), and 1-bromo-3-(2,2,3,3,3-pentafluoropropoxy)benzene (1.90 g, 6.23 mmol, 1.00 equiv). After stirring for 4 hr at 100° C., the reaction mixture was concentrated in vacuo and the residue was purified by column chromatography eluting with EtOAc/hexanes to afford 2.1 g of the title compound (83% yield).

NMR Spectroscopy: $^1$H NMR (300 MHz, $CDCl_3$, 23° C., δ): 8.01 (d, J=8.4 Hz, 1H), 7.65-7.25 (m, 5H), 7.08 (d, J=8.1 Hz, 1H), 6.79 (dd, J=8.4 Hz, 2.4 Hz, 1H), 4.46 (t, J=12 Hz, 2H). $^{19}$F NMR (282 MHz, $CDCl_3$, 23° C., δ): −83.4 (m, 3F), −112.0 (m, 1F), −123.4 (m, 2F).

(S)-2-(1-aminoethyl)-5-fluoro-3-(3-(2,2,3,3,3-pentafluoropropoxy)phenyl)quinazolin-4(3H)-one

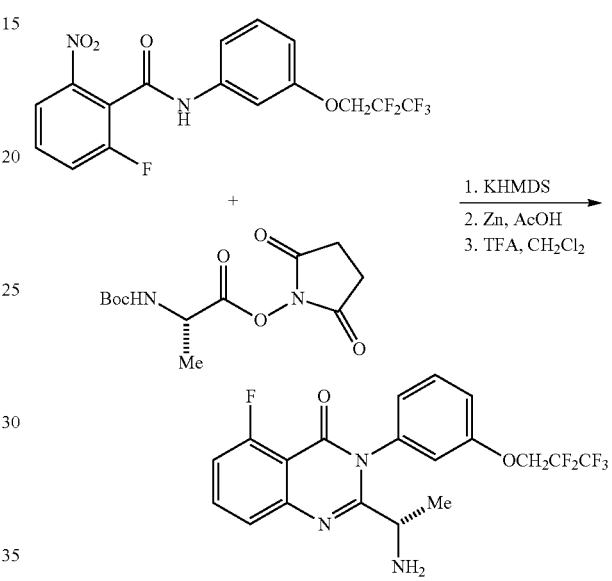

Under nitrogen, to 2-fluoro-6-nitro-N-(3-(2,2,3,3,3-pentafluoropropoxy)phenyl)benzamide (2.1 g, 5.14 mmol, 1.00 equiv) in THF (25 mL) at −78° C. was added KHMDS (1.0 M in THF, 5.14 mL, 5.1 mmol, 1.0 equiv). After stirring for 20 min at −78° C., (S)-2,5-dioxopyrrolidin-1-yl 2-((tert-butoxycarbonyl)amino)propanoate (1.62 g, 5.65 mmol, 1.10 equiv) was added to the reaction mixture. After stirring for 1 hr at 0° C., water (30 mL) was added to the reaction mixture. The phases were separated and the aqueous phase was extracted with EtOAc (3×30 mL). The combined organic phases were washed with brine (50 mL) and dried ($MgSO_4$). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (9 mL) at 23° C. was added Zn powder (6.77 g, 104 mmol, 20.1 equiv). After stirring for 1.5 hr at 23° C., the reaction mixture was filtered and the filtrate was concentrated in vacuo to afford a crude quinazolinone, which was used in the next step without further purification.

Under nitrogen, to the crude material obtained above in $CH_2Cl_2$ (5.0 mL) at 23° C. was added TFA (5.0 mL). After stirring for 30 min at 23° C., the reaction mixture was concentrated in vacuo. Aqueous $K_2CO_3$ solution (3.0 mL) was added to the residue and was extracted with $CH_2Cl_2$ (3×3.0 mL). The combined organic phases were washed with brine (3.0 mL) and dried ($MgSO_4$). The filtrate was concentrated in vacuo and the residue was purified by column chromatography on silica gel eluting with hexanes/EtOAc to afford 710 mg of the title compound (32% yield over 3 steps).

NMR Spectroscopy: ¹H NMR (300 MHz, DMSO-d6, 23° C., δ): 8.20-7.81 (m, 3H), 7.62-7.48 (m, 2H), 7.41-7.08 (m, 4H), 5.00-4.79 (m, 2H), 4.00-3.79 (m, 1H), 1.34-1.26 (m, 3H). ¹⁹F NMR (282 MHz, DMSO-d6, 23° C., δ): −82.6 (m, 3F), −110.7 (m, 1F), −122.5 (m, 2F).

(S)-2-(1-((7H-pyrrolo[2,3-d]pyrimidin-4-yl)amino)ethyl)-5-fluoro-3-(3-(2,2,3,3,3-pentafluoropropoxy)phenyl)quinazolin-4(3H)-one

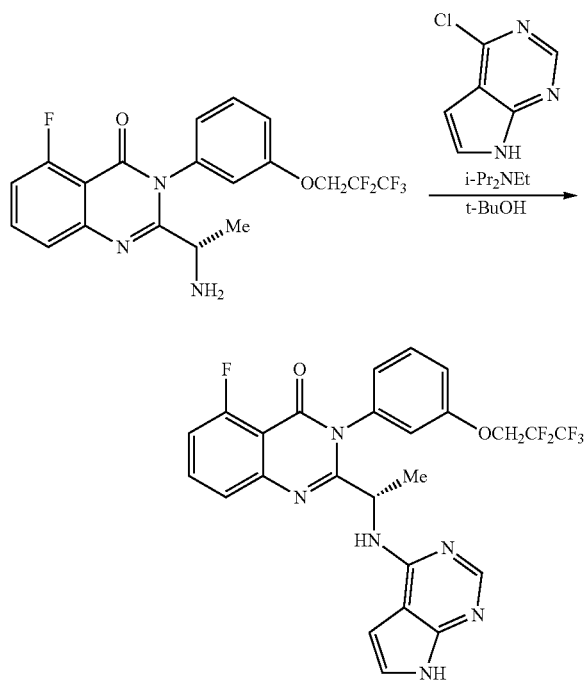

Under nitrogen, to (S)-2-(1-aminoethyl)-5-fluoro-3-(3-(2,2,3,3,3-pentafluoropropoxy)phenyl)quinazolin-4(3H)-one (86 mg, 0.20 mmol, 1.0 equiv) in t-BuOH (0.2 mL) at 23° C. was added 4-chloro-7H-pyrrolo[2,3-d]pyrimidine (34 mg, 0.22 mmol, 1.1 equiv) and diisopropylethylamine (70 µL, 0.40 mmol, 2.0 equiv). After stirring for 36 hr at 120° C. in a sealed tube, the reaction mixture was concentrated in vacuo and the residue was purified by preparative TLC eluting with CH₂Cl₂/MeOH to afford 12 mg of the title compound (11% yield).

NMR Spectroscopy: ¹H NMR (300 MHz, CD₃OD, 23° C., δ): 8.00-7.94 (m, 1H), 7.80-7.70 (m, 1H), 7.56-7.42 (m, 2H), 7.32-7.00 (m, 5H), 6.58 (s br, 1H), 5.20-5.04 (m, 1H), 4.69-4.48 (m, 1H), 4.41-3.92 (m, 1H), 1.61-1.55 (m, 3H). ¹⁹F NMR (282 MHz, CD₃OD, 23° C., δ): −84.9 (m, 3F), −112.4 (m, 1F), −124.9 (m, 2F).

Example 1T

Synthesis of (S)-2-(1-((7H-pyrrolo[2,3-d]pyrimidin-4-yl)amino)ethyl)-5-chloro-3-(3-(2,2,2-trifluoroethoxy)phenyl)quinazolin-4(3H)-one (Compound 20A)

2-chloro-6-nitro-N-(3-(2,2,2-trifluoroethoxy)phenyl)benzamide

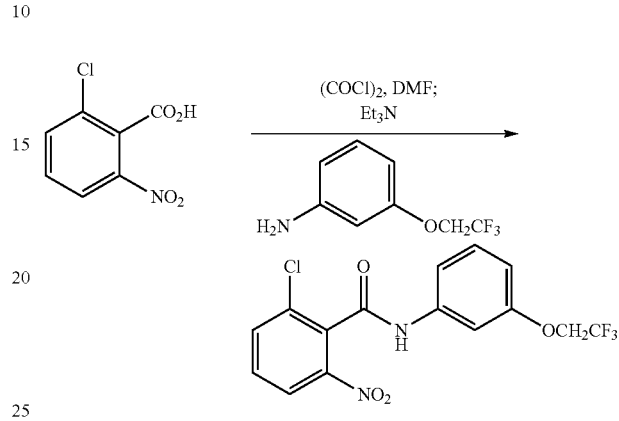

Under nitrogen, to 2-chloro-6-nitrobenzoic acid (1.27 g, 6.28 mmol, 1.00 equiv) in CH₂Cl₂ (20 mL) at 23° C. was added oxalyl chloride (0.585 mL, 6.91 mmol, 1.10 equiv) and DMF (16 µL, 0.19 mmol, 3.0 mol %). After stirring for 1 hr at 23° C., the reaction mixture was cooled to 0° C. and triethylamine (2.63 mL, 18.8 mmol, 3.00 equiv) and 3-(2,2,2-trifluoroethoxy)aniline (1.20 g, 6.28 mmol, 1.00 equiv) were added. After stirring for 15 min at 0° C., 3N HCl aq (50 mL) was added. The phases were separated and the aqueous phase was extracted with CH₂Cl₂ (3×3.0 mL). The combined organic phases were washed with brine (3.0 mL) and dried (MgSO₄). The filtrate was concentrated in vacuo and the residue was purified by column chromatography on silica gel eluting with hexanes/EtOAc to afford 965 mg of the title compound (41% yield).

NMR Spectroscopy: ¹H NMR (300 MHz, CDCl₃, 23° C., δ): 8.16 (d, J=8.4 Hz, 1H), 7.79 (d, J=8.4 Hz, 1H), 7.62-7.27 (m, 4H), 7.09 (d, J=8.1 Hz, 1H), 6.79 (dd, J=8.4 Hz, 2.4 Hz, 1H), 4.38 (q, J=8.1 Hz, 2H). ¹⁹F NMR (282 MHz, CDCl₃, 23° C., δ): −73.9 (t, J=8.1 Hz, 3F).

(S)-2-(1-aminoethyl)-5-chloro-3-(3-(2,2,2-trifluoroethoxy)phenyl)quinazolin-4(3H)-one

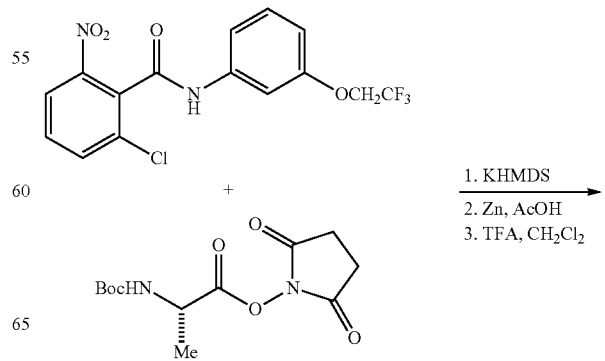

73
-continued

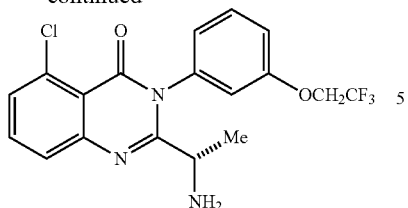

Under nitrogen, to 2-chloro-6-nitro-N-(3-(2,2,2-trifluoroethoxy)phenyl)benzamide (965 mg, 2.57 mmol, 1.00 equiv) in THF (25 mL) at −78° C. was added KHMDS (1.0 M in THF, 2.57 mL, 2.6 mmol, 1.0 equiv). After stirring for 20 min at −78° C., (S)-2,5-dioxopyrrolidin-1-yl 2-((tert-butoxycarbonyl)amino)propanoate (810 mg, 2.83 mmol, 1.10 equiv) was added to the reaction mixture. After stirring for 1 hr at 0° C., water (30 mL) was added to the reaction mixture. The phases were separated and the aqueous phase was extracted with EtOAc (3×30 mL). The combined organic phases were washed with brine (50 mL) and dried (MgSO₄). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (6 mL) at 23° C. was added Zn powder (2.51 g, 38.4 mmol, 15.0 equiv). After stirring for 1.5 hr at 23° C., the reaction mixture was filtered and the filtrate was concentrated in vacuo to afford a crude quinazolinone, which was used in the next step without further purification.

Under nitrogen, to the crude material obtained above in CH₂Cl₂ (10 mL) at 23° C. was added TFA (10 mL). After stirring for 30 min at 23° C., the reaction mixture was concentrated in vacuo. Aqueous K₂CO₃ solution (3.0 mL) was added to the residue and was extracted with CH₂Cl₂ (3×3.0 mL). The combined organic phases were washed with brine (3.0 mL) and dried (MgSO₄). The filtrate was concentrated in vacuo and the residue was purified by column chromatography on silica gel eluting with hexanes/EtOAc to afford 320 mg of the title compound (31% yield over 3 steps).

NMR Spectroscopy: ¹H NMR (300 MHz, CDCl₃, 23° C., δ): 7.63-7.28 (m, 3H), 7.15-6.65 (m, 4H), 4.36 (q, J=8.4 Hz, 2H) 3.71-3.59 (m, 1H), 1.71 (s br, 2H), 1.45-1.35 (m, 3H). ¹⁹F NMR (282 MHz, CDCl₃, 23° C., δ): −73.9 (m, 3F).

(S)-2-(1-((7H-pyrrolo[2,3-d]pyrimidin-4-yl)amino)ethyl)-5-chloro-3-(3-(2,2,2-trifluoroethoxy)phenyl)quinazolin-4(3H)-one

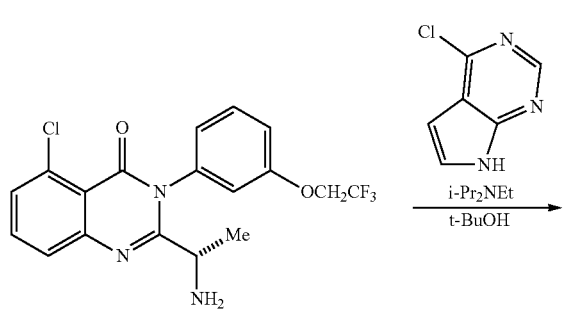

74
-continued

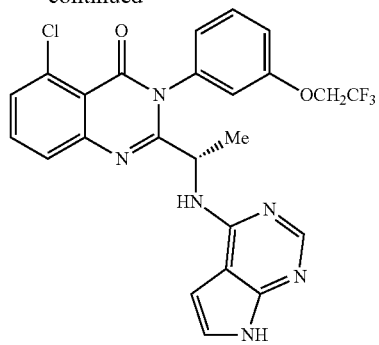

Under nitrogen, to (S)-2-(1-aminoethyl)-5-chloro-3-(3-(2,2,2-trifluoroethoxy)phenyl)quinazolin-4(3H)-one (80 mg, 0.20 mmol, 1.0 equiv) in t-BuOH (0.2 mL) at 23° C. was added 4-chloro-7H-pyrrolo[2,3-d]pyrimidine (34 mg, 0.22 mmol, 1.1 equiv) and diisopropylethylamine (70 μL, 0.40 mmol, 2.0 equiv). After stirring for 28 hr at 120° C. in a sealed tube, the reaction mixture was concentrated in vacuo and the residue was purified by preparative TLC eluting with CH₂Cl₂/MeOH to afford 15 mg of the title compound (15% yield).

NMR Spectroscopy: ¹H NMR (300 MHz, CD₃OD, 23° C., δ): 8.02-7.90 (m, 1H), 7.70-7.58 (m, 2H), 7.50-7.40 (m, 2H), 7.24-6.97 (m, 4H), 6.56 (s br, 1H), 5.21-5.02 (m, 1H), 4.60-4.42 (m, 1H), 4.27-3.80 (m, 1H), 1.56 (d, J=6.6 Hz, 3H). ¹⁹F NMR (282 MHz, CD₃OD, 23° C., δ): −75.6 (m, 3F).

Example 1U

Synthesis of 2-(((7H-pyrrolo[2,3-d]pyrimidin-4-yl)amino)methyl)-5-fluoro-3-(3-(2,2,2-trifluoroethoxy)phenyl)quinazolin-4(3H)-one (Compound 21A)

2-(aminomethyl)-5-fluoro-3-(3-(2,2,2-trifluoroethoxy)phenyl)quinazolin-4(3H)-one

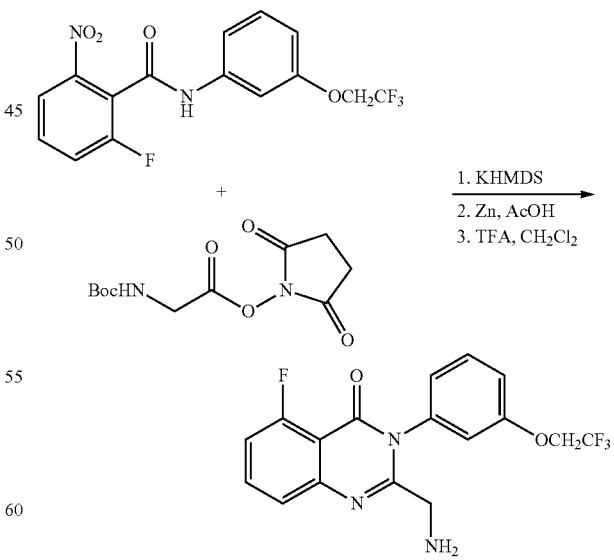

Under nitrogen, to 2-fluoro-6-nitro-N-(3-(2,2,2-trifluoroethoxy)phenyl)benzamide (1.60 g, 4.47 mmol, 1.00 equiv) in THF (20 mL) at −78° C. was added KHMDS (1.0 M in THF, 4.47 mL, 4.5 mmol, 1.0 equiv). After stirring for 20 min at −78° C., 2,5-dioxopyrrolidin-1-yl 2-((tert-butoxycarbonyl)amino)acetate (1.22 g, 4.47 mmol, 1.00 equiv) was added to the reaction mixture. After stirring for 1 hr at 0° C., water (30 mL) was added to the reaction mixture. The phases were separated and the aqueous phase was extracted with EtOAc (3×30 mL). The combined organic phases were washed with brine (50 mL) and dried (MgSO$_4$). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (7 mL) at 23° C. was added Zn powder (2.92 g, 44.7 mmol, 10.0 equiv). After stirring for 1.5 hr at 23° C., the reaction mixture was filtered and the filtrate was concentrated in vacuo to afford a crude quinazolinone, which was used in the next step without further purification.

Under nitrogen, to the crude material obtained above in CH$_2$Cl$_2$ (5.0 mL) at 23° C. was added TFA (5.0 mL). After stirring for 30 min at 23° C., the reaction mixture was concentrated in vacuo. Aqueous K$_2$CO$_3$ solution (3.0 mL) was added to the residue and was extracted with CH$_2$Cl$_2$ (3×3.0 mL). The combined organic phases were washed with brine (3.0 mL) and dried (MgSO$_4$). The filtrate was concentrated in vacuo and the residue was purified by column chromatography on silica gel eluting with hexanes/EtOAc to afford 320 mg of the title compound (18% yield over 3 steps).

NMR Spectroscopy: $^1$H NMR (300 MHz, CDCl$_3$, 23° C., δ): 7.78-7.68 (m, 1H), 7.59-7.48 (m, 2H), 7.18-7.09 (m, 2H), 7.00-6.83 (m, 2H), 4.38 (q, J=8.1 Hz, 2H) 3.51 (s, 2H), 1.77 (s br, 2H). $^{19}$F NMR (282 MHz, CDCl$_3$, 23° C., δ): −73.7 (m, 3F), −109.8 (m, 1F).

2-(((7H-pyrrolo[2,3-d]pyrimidin-4-yl)amino)methyl)-5-fluoro-3-(3-(2,2,2-trifluoroethoxy)phenyl)quinazolin-4(3H)-one

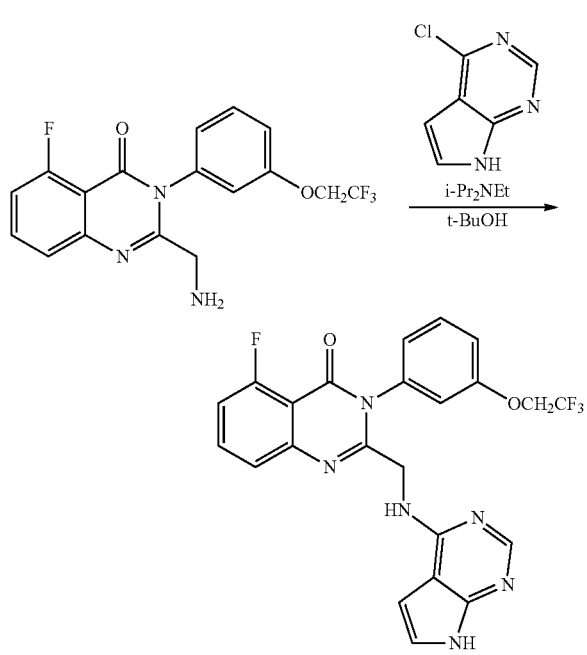

Under nitrogen, to 2-(aminomethyl)-5-fluoro-3-(3-(2,2,2-trifluoroethoxy)phenyl)quinazolin-4(3H)-one (73 mg, 0.20 mmol, 1.0 equiv) in t-BuOH (0.2 mL) at 23° C. was added 4-chloro-7H-pyrrolo[2,3-d]pyrimidine (34 mg, 0.22 mmol, 1.1 equiv) and diisopropylethylamine (70 μL, 0.40 mmol, 2.0 equiv). After stirring for 36 hr at 120° C. in a sealed tube, the reaction mixture was concentrated in vacuo and the residue was purified by preparative TLC eluting with CH$_2$Cl$_2$/MeOH to afford 20 mg of the title compound (21% yield).

NMR Spectroscopy: $^1$H NMR (300 MHz, CD$_3$OD, 23° C., δ): 7.89 (s, 1H), 7.72-7.62 (m, 1H), 7.43-7.35 (m, 3H), 7.19-7.00 (m, 4H), 6.46 (s br, 1H), 4.57-4.30 (m, 4H). $^{19}$F NMR (282 MHz, CD$_3$OD, 23° C., δ): −75.7 (m, 3F), −112.4 (m, 1F).

Example 1V

Synthesis of (S)-2-(1-((7H-pyrrolo[2,3-d]pyrimidin-4-yl)amino)ethyl)-3-(3-(2,2-difluoroethoxy)phenyl)-5-fluoroquinazolin-4(3H)-one (Compound 22A)

N-(3-(2,2-difluoroethoxy)phenyl)-2-fluoro-6-nitrobenzamide

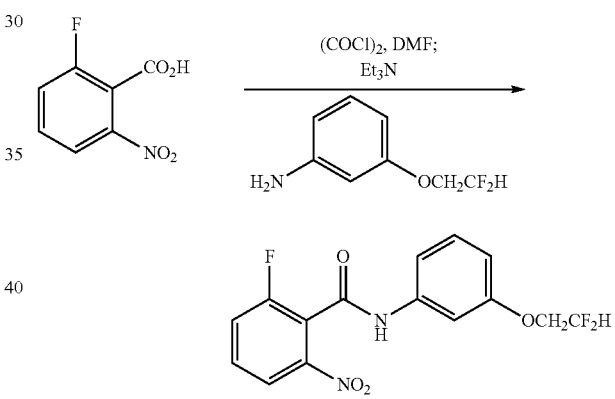

Under nitrogen, to 2-fluoro-6-nitrobenzoic acid (1.27 g, 6.28 mmol, 1.00 equiv) in CH$_2$Cl$_2$ (20 mL) at 23° C. was added oxalyl chloride (0.585 mL, 6.91 mmol, 1.10 equiv) and DMF (16 μL, 0.19 mmol, 3.0 mol %). After stirring for 1 hr at 23° C., the reaction mixture was cooled to 0° C. and triethylamine (2.63 mL, 18.8 mmol, 3.00 equiv) and 3-(2,2-difluoroethoxy)aniline (1.09 g, 6.28 mmol, 1.00 equiv) were added. After stirring for 15 min at 0° C., 3N HCl aq (50 mL) was added. The phases were separated and the aqueous phase was extracted with CH$_2$Cl$_2$ (3×3.0 mL). The combined organic phases were washed with brine (3.0 mL) and dried (MgSO$_4$). The filtrate was concentrated in vacuo and the residue was purified by column chromatography on silica gel eluting with hexanes/EtOAc to afford 1.07 g of the title compound (50% yield).

NMR Spectroscopy: $^1$H NMR (300 MHz, CDCl$_3$, 23° C., δ): 7.99 (d, J=8.4 Hz, 1H), 7.69-7.28 (m, 5H), 7.09 (d, J=8.1 Hz, 1H), 6.78 (dd, J=8.4 Hz, 2.4 Hz, 1H), 6.25-5.90 (m, 1H), 4.29-4.18 (m, 2H).

(S)-2-(1-aminoethyl)-3-(3-(2,2-difluoroethoxy)phe-nyl)-5-fluoroquinazolin-4(3H)-one (S)-2-(1-((7H-pyrrolo[2,3-d]pyrimidin-4-yl)amino)ethyl)-3-(3-(2,2-difluoroethoxy)phenyl)-5-fluoroquinazolin-4(3H)-one

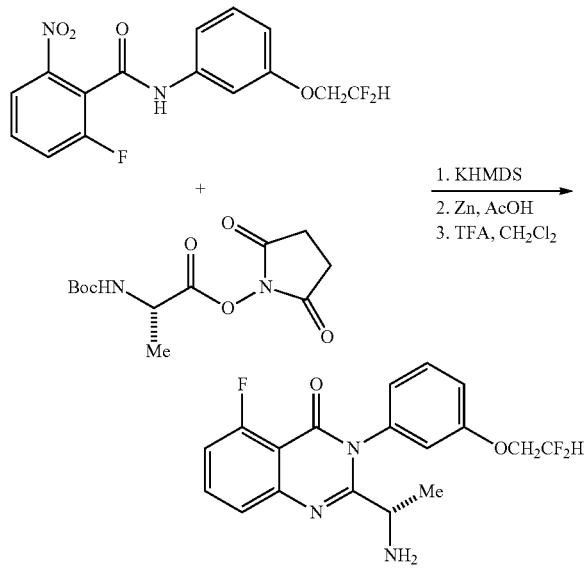

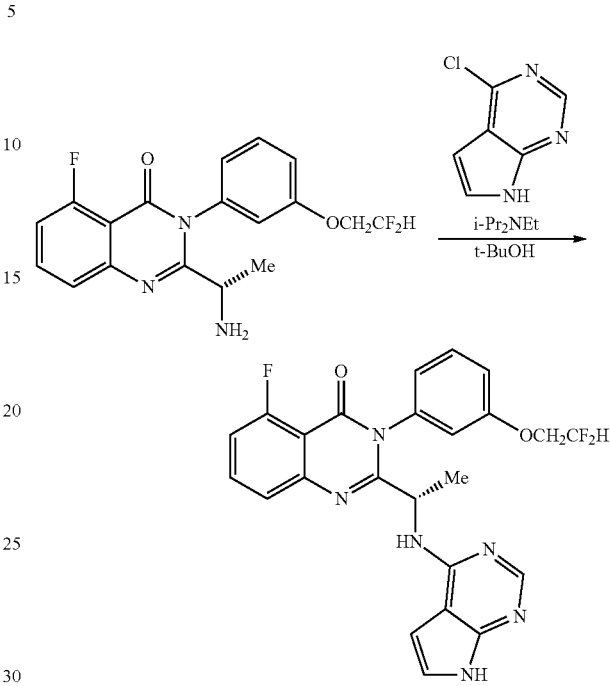

Under nitrogen, to N-(3-(2,2-difluoroethoxy)phenyl)-2-fluoro-6-nitrobenzamide (1.0 g, 2.94 mmol, 1.00 equiv) in THF (25 mL) at −78° C. was added KHMDS (1.0 M in THF, 2.94 mL, 2.9 mmol, 1.0 equiv). After stirring for 20 min at −78° C., (S)-2,5-dioxopyrrolidin-1-yl 2-((tert-butoxycarbonyl)amino)propanoate (842 mg, 2.94 mmol, 1.00 equiv) was added to the reaction mixture. After stirring for 1 hr at 0° C., water (30 mL) was added to the reaction mixture. The phases were separated and the aqueous phase was extracted with EtOAc (3×30 mL). The combined organic phases were washed with brine (50 mL) and dried (MgSO$_4$). The filtrate was concentrated in vacuo and the residue was purified by column chromatography on silica gel eluting with hexanes/EtOAc to afford an imide. The NMR peaks were broad and the structure assignment was not conclusive, but this material was used in the next step without further purification.

Under ambient atmosphere, to the imide prepared above in AcOH (6 mL) at 23° C. was added Zn powder (3.83 g, 58.8 mmol, 20.0 equiv). After stirring for 1.5 hr at 23° C., the reaction mixture was filtered and the filtrate was concentrated in vacuo to afford a crude quinazolinone, which was used in the next step without further purification.

Under nitrogen, to the crude material obtained above in CH$_2$Cl$_2$ (10 mL) at 23° C. was added TFA (10 mL). After stirring for 30 min at 23° C., the reaction mixture was concentrated in vacuo. Aqueous K$_2$CO$_3$ solution (3.0 mL) was added to the residue and was extracted with CH$_2$Cl$_2$ (3×3.0 mL). The combined organic phases were washed with brine (3.0 mL) and dried (MgSO$_4$). The filtrate was concentrated in vacuo and the residue was purified by column chromatography on silica gel eluting with hexanes/EtOAc to afford 300 mg of the title compound (28% yield over 3 steps).

NMR Spectroscopy: $^1$H NMR (300 MHz, CDCl$_3$, 23° C., δ): 7.73-7.68 (m, 1H), 7.53-7.49 (m, 2H), 7.14-7.08 (m, 2H), 6.97-6.86 (m, 2H), 6.25-5.91 (m, 1H), 4.29-4.15 (m, 2H), 3.77-3.69 (m, 1H), 1.66 (s br, 2H), 1.33-1.22 (m, 3H).

Under nitrogen, to (S)-2-(1-aminoethyl)-5-chloro-3-(3-(2,2-trifluoroethoxy)phenyl)quinazolin-4(3H)-one (73 mg, 0.20 mmol, 1.0 equiv) in t-BuOH (0.2 mL) at 23° C. was added 4-chloro-7H-pyrrolo[2,3-d]pyrimidine (34 mg, 0.22 mmol, 1.1 equiv) and diisopropylethylamine (70 µL, 0.40 mmol, 2.0 equiv). After stirring for 28 hr at 120° C. in a sealed tube, the reaction mixture was concentrated in vacuo and the residue was purified by preparative TLC eluting with CH$_2$Cl$_2$/MeOH to afford 20 mg of the title compound (21% yield).

NMR Spectroscopy: $^1$H NMR (300 MHz, CD$_3$OD, 23° C., δ): 8.00-7.91 (m, 1H), 7.81-7.72 (m, 1H), 7.58-7.45 (m, 2H), 7.27-6.98 (m, 5H), 6.59 (s br, 1H), 6.34-5.80 (m, 1H), 5.22-5.08 (m, 1H), 4.34-4.22 (m, 1H), 4.03-3.65 (m, 1H), 1.58 (d, J=6.6 Hz, 3H).

Example 2

Testing of Compounds of the Present Invention for PI3K Inhibitory Activity

Example 2A

Homogeneous Time Resolved Fluorescence Assay

The ability of the compounds of the present invention to inhibit the activity of four PI3K isoforms, PI3Kα, PI3Kβ, PI3Kγ, and PI3Kδ, were determined using a commercially available lipid kinase assay run in Homogeneous Time Resolved Fluorescence (HTRF) format.

Assay Description

Assay principle: The PIP3 product is detected by displacement of biotin-PIP3 from an energy transfer complex consisting of Europium labeled anti-GST monoclonal antibody, a GST-tagged pleckstrin homology (PH) domain, biotinylated PIP3 and Streptavidin-Allophycocyanin (APC). Excitation of Europium in the complex results in an energy transfer to the APC and a fluorescent emission at 665 nm. The PIP3 product formed by PI 3-Kinase(h) activity displaces biotin-PIP3 from the complex resulting in a loss of energy transfer and thus a decrease in signal.

This is a 3-step reaction: First, the kinase reaction with PIP2 substrate is carried out in the presence of ATP, and the reaction is quenched with stop Solution, and then finally detect by adding Detection Mixture followed by incubation.

Reaction Conditions:
Assay Buffer: HEPES 50 mM (pH7.0), NaN3 0.02%, BSA 0.01%, Orthovanadate 0.1 mM, 1% DMSO.
Detection buffer: HEPES 10 mM (pH7.0), BSA 0.02%, KF 0.16 M, EDTA 4 mM.
Substrate: 10 μM PIP2 substrate (PI(4,5)P2)
ATP: 10 μM ATP under standard conditions
Control Inhibitor: PI-103

Assay Procedure:
1. Prepare substrate in freshly prepared Reaction Buffer
2. Deliver kinase into the substrate solution and gently mix
3. Deliver compounds in 100% DMSO into the kinase reaction mixture by Acoustic technology (Echo550; nano-litter range), incubate for 10 min at room temp
4. Deliver ATP into the reaction mixture to initiate the reaction
5. Incubate for 30 min at 30° C.
6. Quench the reaction with Stop Solution.
7. Add Detection Mixture, and incubate for overnight.
8. Measure HTRF: Ex=320 nm, ratio of Em=615 nm and Em=665 nm.

Data Analysis:
The emission ratio is converted into μM PIP3 production based on PIP3 standard curves. The nonlinear regression to obtain the standard curve and $IC_{50}$ values are performed using Graphpad Prism software. The $IC_{50}$ values for the compounds of the present invention tested in this assay are shown in Table 2.

| Compound No. | PI3Kα | PI3Kβ | PI3Kγ | PI3Kδ |
|---|---|---|---|---|
| | $IC_{50}$ ($10^{-6}$ M) | | | |
| 2A | | 3.9 | 1.8 | 0.08 |
| 1A | 3.7 | 0.65 | 1.2 | 0.008 |
| 6A | 15 | 3.1 | 0.3 | 0.02 |
| 7A | 28 | 5.8 | 1.3 | 0.05 |
| 10A | | | 0.74 | 0.02 |
| 11A | 115 | | 3 | 0.11 |
| 15A | 9.7 | 7.3 | 0.74 | 0.009 |
| 16A | | 10.5 | 5.4 | 0.09 |
| 17A | 10 | 3.4 | 1.2 | 0.008 |
| 19A | >10 | >10 | 4.5 | 0.19 |
| 20A | 4.1 | 1.1 | 0.46 | 0.01 |
| 21A | | >10 | | 2.1 |

Example 2B

Reporter Displacement Assay

The ability of the compounds of the present invention to inhibit the activity of four PI3K isoforms, PI3Kα, PI3Kβ, PI3Kγ, and PI3Kδ, were determined using the commercially available reporter displacement assay that is based on reporter probes that are designed to bind to the site of interest of the target protein. The proximity between reporter and protein results in the emission of an optical signal. Compounds that bind to the same site as the reporter probe displace the probe, causing signal diminution. Reporter displacement is measured over time after addition of compounds at various concentrations. The assay conditions were:

PI3Kα human fl; BPS #40621
PI3Kβ human (1-1070); Carna biosciences #11-102
PI3Kγ human (144-1102); Proteros
PI3Kδ human fl; BPS #40628
Reaction volume: 10 μL
Reaction temperature: RT
Assay plates: 384 well U bottom, PP, black, low volume (Corning, 3676)

Controls
Full probe displacement: absence of enzyme and compound
Full probe binding: absence of compound
Reaction buffer: 20 mM Mops, pH 7.01 mM DTT, 0.01% Tween 20

Compound 22A was tested in this assay and was determined to have the following $IC_{50}$ values ($10^{-6}$ M): PI3Kα—9.8; PI3Kβ—2.1, PI3Kγ—1.2, PI3Kδ—0.02.

The compounds of the present invention are shown to be selective for PI3Kδ over the other three isoforms.

EQUIVALENTS

Those skilled in the art will recognize, or be able to ascertain using no more than routine experimentation, many equivalents to the specific embodiments and methods described herein. Such equivalents are intended to be encompassed by the scope of the present invention.

All patents, patent applications, and literature references cited herein are hereby expressly incorporated by reference.

The invention claimed is:
1. A method of inhibiting a PI3 kinase in a subject in need thereof, comprising administering to the subject a therapeutically effective amount of a compound of Formula I:

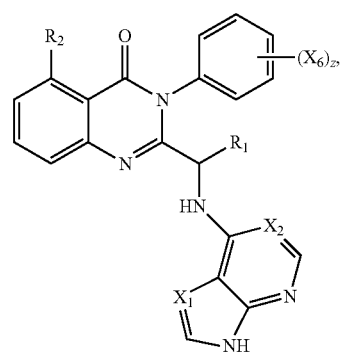

(I)

or a pharmaceutically acceptable salt or solvate thereof, wherein
$X_1$ is selected from N, CH, CF, $CCF_3$, $CCHF_2$, and $CCH_2F$;
$X_2$ is N or CH;
$R_1$ is $(CX_{3A}X_{4A})_s$—$(O)_v$—$(CX_{3B}X_{4B})_t$—$(O)_w$—$(CX_{3C}X_{4C})_u$—$(O)_x$—$X_5$;
$X_{3A}$, $X_{3B}$, $X_{3C}$, $X_{4A}$, $X_{4B}$, and $X_{4C}$ are each independently selected from H and F;
$X_5$ is selected from H, F, $CF_3$, $CHF_2$, $CH_2F$, $OCF_3$, $OCHF_2$, $OCH_2F$, $OCH_2CF_3$, $OCH_2CHF_2$, and $OCH_2CH_2F$;
s, t, and u are each independently selected from 0, 1, 2, 3, 4, 5, 6, and 7;
v, w, and x are each independently selected from 0 and 1;
$R_2$ is Cl or F;

each $X_6$ is independently $(CX_{7A}X_{8A})_e$—$(O)_h$—$(CX_{7B}X_{8B})_f$—$(O)_i$—$(CX_{7C}X_{8C})_g$—$(O)_j$—$X_9$;

$X_{7A}$, $X_{7B}$, $X_{7C}$, $X_{8A}$, $X_{8B}$, and $X_{8C}$ are each independently selected from H and F;

$X_9$ is selected from H, F, $CF_3$, $CHF_2$, $CH_2F$, $OCF_3$, $OCHF_2$, $OCH_2F$, $OCH_2CF_3$, $OCH_2CHF_2$, and $OCH_2CH_2F$;

e, f, and g are each independently selected from 0, 1, 2, 3, 4, 5, 6, and 7;

h, i, and j are each independently selected from 0 and 1; and z is selected from 0, 1, and 2, provided that when $X_1$ and $X_2$ are each N and z is 0, then $R_1$ comprises at least one F atom; and that when $X_1$ and $X_2$ are each N and $R_2$ is Cl, then z is 1 or 2 and $X_9$ is selected from $CF_3$, $CHF_2$, $CH_2F$, $OCF_3$, $OCHF_2$, $OCH_2F$, $OCH_2CF_3$, $OCH_2CHF_2$, and $OCH_2CH_2F$, and provided that $R_1$ does not contain a total number of more than 8 atoms of carbon and oxygen and $R_1$ does not contain adjacent oxygen atoms, and that each $X_6$ does not contain a total number of more than 8 atoms of carbon and oxygen and $X_6$ does not contain adjacent oxygen atoms.

2. The method of claim 1, wherein the compound is of Formula Ia:

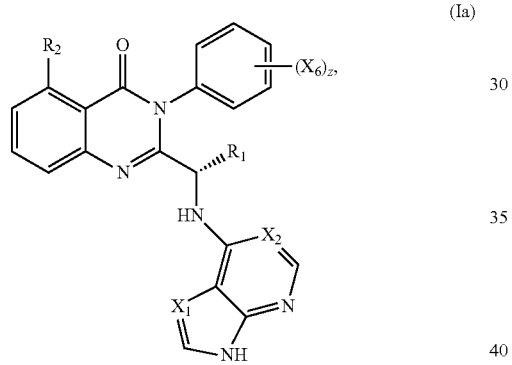

(Ia)

or a pharmaceutically acceptable salt or solvate thereof.

3. The method of claim 1, wherein $R_2$ is F.
4. The method of claim 1, wherein $X_1$ is N and $X_2$ is N or CH.
5. The method of claim 1, wherein $X_1$ is CH, CF, or $CCF_3$ and $X_2$ is N or CH.
6. The method of claim 1, wherein the sum of $v+w+x \leq 2$.
7. The method of claim 1, wherein the sum of $s+t+u \leq 6$.
8. The method of claim 1, wherein $X_5$ is H, $CF_3$, $CHF_2$, or $CH_2F$.
9. The method of claim 1, wherein z is 0 or 1.
10. The method of claim 9, wherein

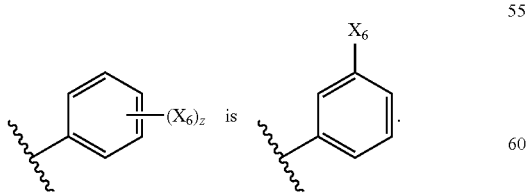

11. The method of claim 1, wherein the sum of $h+i+j \leq 2$.
12. The method of claim 11, wherein h is 1; i is 0; and j is 0.
13. The method of claim 1, wherein the sum of $e+f+g \leq 6$.

14. The method of claim 1, wherein $X_9$ is $CF_3$, $CHF_2$, $CH_2F$, $OCF_3$, $OCHF_2$, $OCH_2F$, $OCH_2CF_3$, $OCH_2CHF_2$, or $OCH_2CH_2F$.

15. The method of claim 1, wherein the compound is selected from the group consisting of:

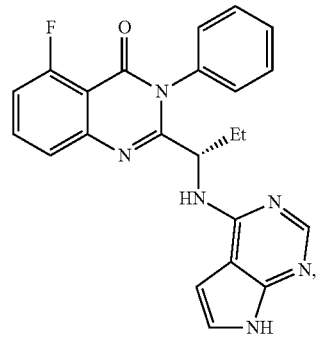

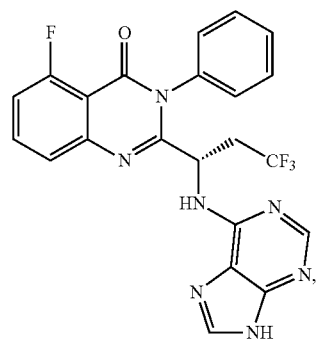

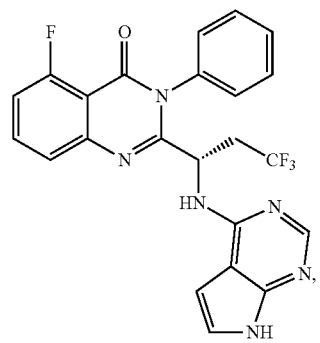

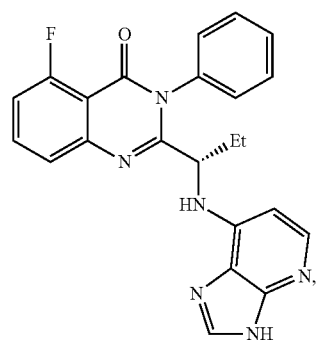

83
-continued
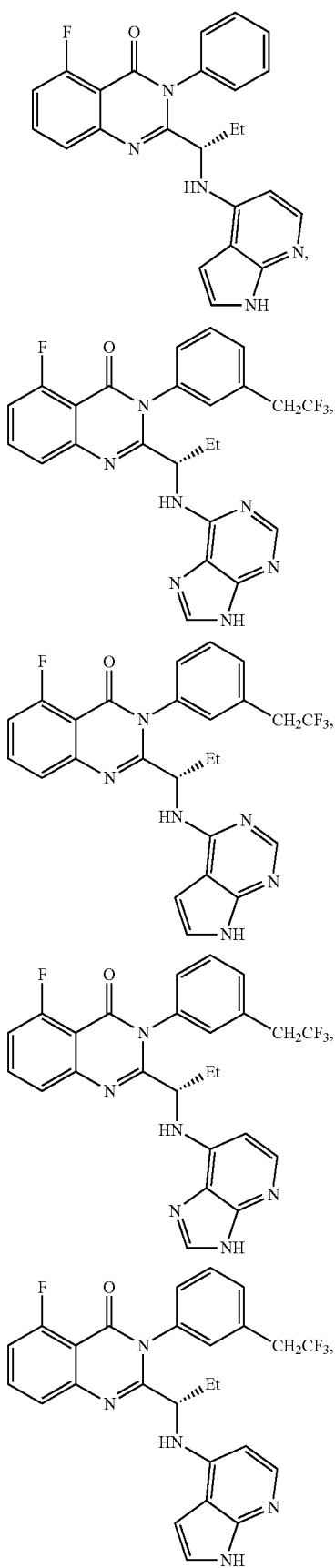
84
-continued
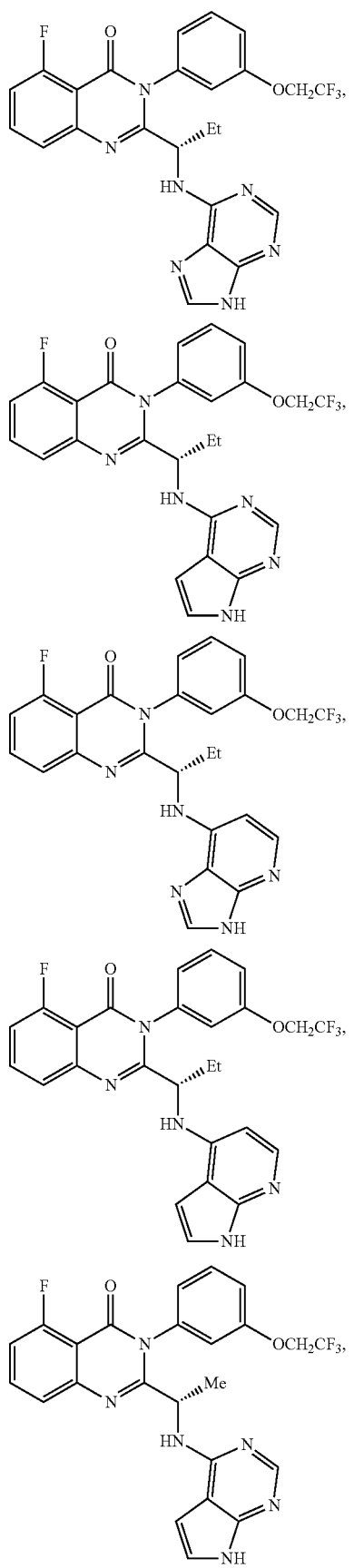

-continued
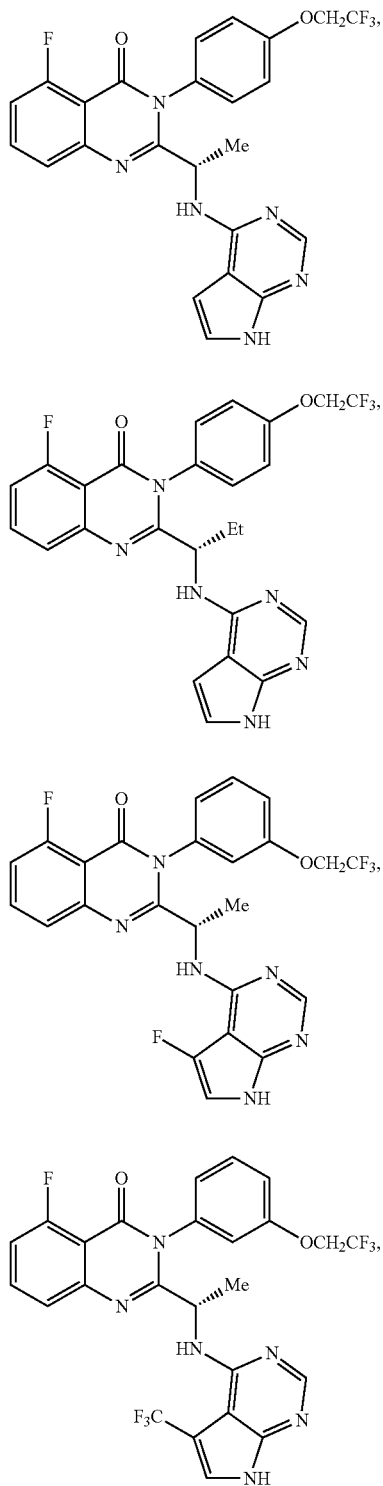
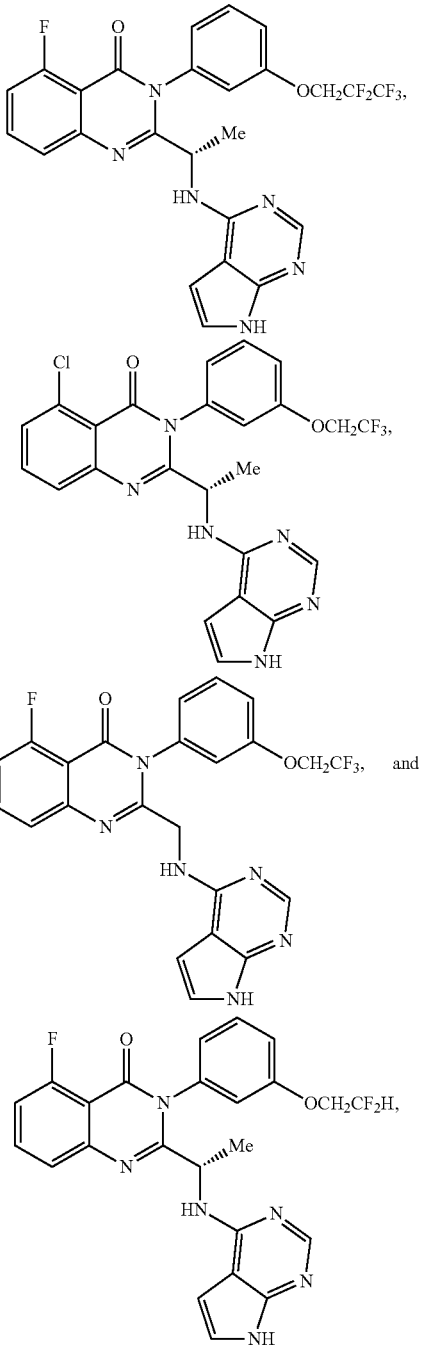
or a pharmaceutically acceptable salt or solvate thereof.
16. The method of claim 1, wherein the PI3 kinase is PI3Kα, PI3Kβ, PI3Kγ, or PI3Kδ.
17. The method of claim 1, wherein the PI3 kinase is PI3Kδ.
* * * * *